US006194186B1

(12) United States Patent
Lal et al.

(10) Patent No.: US 6,194,186 B1
(45) Date of Patent: Feb. 27, 2001

(54) HUMAN PROTEIN KINASE AND KINASE INHIBITORS

(75) Inventors: Preeti Lal, Santa Clara; Jennifer L. Hillman, Mountain View; Olga Bandman, Mountain View; Neil C. Corley, Mountain View; Purvi Shah, Sunnyvale, all of CA (US)

(73) Assignee: Incyte Pharmaceuticals, Inc., Palo Alto, CA (US)

( * ) Notice: Subject to any disclaimer, the term of this patent is extended or adjusted under 35 U.S.C. 154(b) by 0 days.

(21) Appl. No.: 08/977,816

(22) Filed: Nov. 25, 1997

(51) Int. Cl.$^7$ .............................. C12N 9/12; C12N 1/20; C12N 15/00; C07H 21/04
(52) U.S. Cl. ..................... 435/194; 435/69.1; 435/252.3; 435/320.1; 435/69.2; 435/15; 435/6; 536/23.2; 536/23.5; 530/350; 514/44
(58) Field of Search .................................. 435/194, 69.1, 435/252.3, 320.1, 6, 15, 69.2; 536/23.2, 23.5; 530/350; 514/44

(56) References Cited

PUBLICATIONS

Day, M.L., et al., "Phorbol Ester–induced Apoptosis is Accompanied by NGFI–A and c–fos Activation in Androgen–sensitive Prostate Cancer Cells," *Cell Growth Differentiation*, 5(7):735–741 (1994).
Powell, C.T., et al., "Persistent Membrane Translocation of protein Kinase C alpha during 12–0–Tetradecanoylporbol–13–acetate–induced Apoptosis of LNCaP Human Prostate Cancer Cells," *Cell Growth differentiation*, 7:419–428 (1996).
Lee, T.G., et al., "The 58,000–Dalton Cellular Inhibitor of the Interferon–Induced Double–Stranded RNA–Activated Protein Kinase (PKR) Is A Member of the Tetratricopeptide Repeat Family of Proteins," *Molecular and Cellular Biology*, 14(4):2331–2342 (1994) (GI 468011 & 468012).
Lock, R.B., et al., "Potentiation of etoposide–induced apoptosis by staurosporine in human tumor cells is associated with events downstreamof DNA–protein complex formation," *Cancer Chemother Pharmacol*, 39:399–409 (1997).
Wilson, R., et al.,(GI 1419440), GenBank Sequence Database (Accession Z75711), National Center for Biotechnology Information, National Library of Medicine, Bethesda, Maryland 20894.

Wilson, R., et al., (GI 1419436), GenBank Sequence Database (Accession Z75711), National Center for Biotechnology Information, National Library of Medicine, Bethesda, Maryland 20894.
Lee, T.G. et al., (GI 468012), GenBank Sequence Database (Accession U04631), National Center for Biotechnology Information, National Library of Medicine, Bethesda, Maryland 20894.
Lee, T.G. et al., (GI 468011), GenBank Sequence Database (Accession U04631), National Center for Biotechnology Information, National Library of Medicine, Bethesda, Maryland 20894.
Scarpetta, M.A. and Uhler, M.D., (GI 200497), GenBank SequenceDatabase (Accession L02241), National Center for Biotechnology Information, National Library of Medicine, Bethesda, Maryland, 20894.
Scarpetta, M.A. and Uhler, M.D., (GI 200496), GenBank SequenceDatabase (Accession L02241), National Center for Biotechnology Information, National Library of Medicine, Bethesda, Maryland, 20894.
Scarpetta, M.A. Uhler, M.D., "Evidence for Two Additional Isoforms of the Endogenous Protein Kinase Inhibitor of cAMP–dependent Protein Kinase in Mouse,"*J. Biol. Chem.*, 268(15) 10927–10931 (1993).
Glass, D.B., et al., "Differential and Common Recognition of the Catalytic Sites of the cGMP–dependent and cAMP––dependent Protein Kinase by Inhibitory Peptides Derived from the Heat–Stable Inhibitor Protein," *J. Biol. Chem.*, 261(26):12166–12171.
Wu, M.,et al., "Serine/Threonine Kinase Activity Associated with the Cytoplasmic Domain of the Lymphotoxin–β Receptor in HepG2 Cells," *The Journal of Biological Chemistry*, 272 (27)17154–17159 (1997).

*Primary Examiner*—Robert A. Wax
*Assistant Examiner*—Tekchand Saidha
(74) *Attorney, Agent, or Firm*—Incyte Pharmaceuticals, Inc.

(57) ABSTRACT

The invention provides a human protein kinase (PK) and kinase inhibitors (PKI) and polynucleotides which identify and encode PK and PKI. The invention also provides expression vectors, host cells, agonists, antibodies and antagonists. The invention also provides methods for diagnosing, treating or preventing disorders associated with expression of PK and PKI.

10 Claims, 25 Drawing Sheets

```
5' TGT AAA ATA GAG GTA ATA ATC CCA GTC CTG CTC ACT GTG TAG ATT TGT GAG GCC       54

63                                                                          108
   CAA ATG AGA GAA AAA AGA CTC GAG AAA CCC TTG TGA ACT AGA ACG TGC AGA AAG 117                                                                          162
   CAA AGG GGT AAG ACA TCA GAC TCT TCC CTA AAC GTG CTC TCT GGG CAC CCC TGA 171                                                                          216
   ACT TGC TCA TCC GGG TTC CCC CTC CCA CAG CAC CAG CAC TTT CTG CAG CTA GAG CTG ATT 225                                                                          270
   AAT GGG CGC TTG AGT GCC TCC TTG CAC TCC CAT GAC ACA GAG ACA CGG GCC 279                                                                          324
   ACC ATG AAC TTG GCA CTG CTG GCT GGT GAC ATC CTT GCT GCA GGG GCA GAT GCC CAC
        M   N   L   A   L   L   A   G   D   I   L   A   A   G   A   D   A   H 333                                                                          378
   TGT CAG CTC CTG CGC TTC CAG GCA CAT CAA CAG CAG GGC AAC AAG GCA GAG AAG
    C   Q   L   L   R   F   Q   A   H   Q   Q   Q   G   N   K   A   E   K 387                                                                          432
   GCC GGT TCC AAG GAG CAG GGG CCT CGA CAA AGG AAG GGA GCA GCC CCA GCA GAG
    A   G   S   K   E   Q   G   P   R   Q   R   K   G   A   A   P   A   E
```

FIGURE 1A

```
441             450             459             468             477             486
AAG AAA TGT GGA GCG GAA ACC CAG CAC GAG GGG CTA GAA CTC AGG GTA GAG AAT
 K   K   C   G   A   E   T   Q   H   E   G   L   E   L   R   V   E   N 495             504             513             522             531             540
TTG CAG GCG GTG CAG GAC TTT AGC TCC GAT CCA CTG CAG AAA GTT GTG TGC
 L   Q   A   V   Q   D   F   S   S   D   P   L   Q   K   V   V   C 549             558             567             576             585             594
TTC AAC CAC GAT AAT ACC CTG CTT GCC ACT GGA ACA GAT GGC TAC GTC CGT
 F   N   H   D   N   T   L   L   A   T   G   T   D   G   Y   V   R 603             612             621             630             639             648
GTC AAG GTG CCC AGC CTG GAG GTT CTG GAG TTC AAA GCC CAC GAA GGG
 V   K   V   P   S   L   E   V   L   E   F   K   A   H   E   G 657             666             675             684             693             702
GAG ATT GAA GAC CTG GCT TTA GGG CCT GAT GGC AAG TTG GTA ACC GTG GGC CGG
 E   I   E   D   L   A   L   G   P   D   G   K   L   V   T   V   G   R 711             720             729             738             747             756
GAC CTT AAG GCC TCT GTG TGG CAG AAG GAT CAG CTG GTG ACA CAG CTG CAC TGG
 D   L   K   A   S   V   W   Q   K   D   Q   L   V   T   Q   L   H   W
```

FIGURE 1B

```
                765       774       783       792       801       810
CAA GAA AAT GGA CCC ACC TTT TCC AGC ACA CCT TAC CGC TAC CAG GCC TGC AGG
 Q   E   N   G   P   T   F   S   S   T   P   Y   R   Y   Q   A   C   R 819       828       837       846       855       864
TTT GGG CAG GTT CCA GAC CAG CCT GCT GGC CTG CGA CTC TTC ACA GTG CAA ATT
 F   G   Q   V   P   D   Q   P   A   G   L   R   L   F   T   V   Q   I 873       882       891       900       909       918
CCC CAC AAG CGC CTG CGC CAG CCC CCT CCC TGC TAC CTC ACA GCC TGG GAT GGC
 P   H   K   R   L   R   Q   P   P   P   C   Y   L   T   A   W   D   G 927       936       945       954       963       972
TCC AAC TTC TTG CCC CTT CGG ACC AAG TCC TGT GGC CAT GAA GTC GTC TCC TGC
 S   N   F   L   P   L   R   T   K   S   C   G   H   E   V   V   S   C 981       990       999      1008      1017      1026
CTC GAT GTC AGT GAA TCC GGC ACC TTC CTC CTA GGC CTG ACA GTC ACT GGC TCT
 L   D   V   S   E   S   G   T   F   L   L   G   L   T   V   T   G   S 1035      1044      1053      1062      1071      1080
GTT GCC ATC TAC ATA GCT TTC TCT CTC CAG TGC CTC TAC TAC AGG GAG GAG GCC
 V   A   I   Y   I   A   F   S   L   Q   C   L   Y   Y   R   E   E   A
```

FIGURE 1C

```
      1089            1098            1107            1116            1125            1134
CAT GGC ATT GTG GTG ACG GAT GTG GCC TTT CTA CCT GAG AAG GGT CGT GGT CCA
 H   G   I   V   V   T   D   V   A   F   L   P   E   K   G   R   G   P
      1143            1152            1161            1170            1179            1188
GAG CTC CTT GGG TCC CAT GAA ACT GCC CTG TTC TCT GTG GCT GTG GAC AGT CGT
 E   L   L   G   S   H   E   T   A   L   F   S   V   A   V   D   S   R
      1197            1206            1215            1224            1233            1242
TGC CAG CTG CAT CTG TTG CCC TCA CGG CGG AGT GTT CCT GTG TGG CTC CTG CTC
 C   Q   L   H   L   L   P   S   R   R   S   V   P   V   W   L   L   L
      1251            1260            1269            1278            1287            1296
CTG TGT GTC GGG CTT ATT ATT GTG ACC ATC CTG CTG CAG AGT GCC TTT
 L   C   V   G   L   I   I   V   T   I   L   L   Q   S   A   F
      1305            1314            1323            1332            1341            1350
CCA GGT TTC CTT TAG CCC TGC TTC CTG GGA ATC AGG AGC CTG GAC ACT GCC
 P   G   F   L   *
      1359            1368            1377            1386            1395            1404
ATC TCT AGA GCA GAG TGG AGG CCT GGA CTC CCT TTG CTC ACT CCA TTC GGG TCC
      1413            1422            1431            1440            1449            1458
ACA GCT GAG GTT GCC TCT GAC AAG ATG AAT GGG CAC TGC CTG CCC TTC TAG TGA
```

FIGURE 1D

```
        1467            1476            1485            1494            1503            1512
AAA GGC TTG GCT ATG GCC CTG TGT GAC TCC AGG TCC AGG GAA CCT TGC CTT CGT
        1521            1530            1539            1548            1557            1566
CAT CTG TGG ATC CAT CCA GAA CAG CGG TAT CTG AAG CCC AGG CCA TAC TCC CTG
        1575            1584            1593            1602            1611            1620
CCT CCT TTC TTC TGC CTA CCA GAG GCT CCA GAG TTG AGC TTG TCC TTA TCT AGA
        1629            1638            1647            1656            1665            1674
AAC ATG TGA AGA TGC CCA AGA GCC TGG AGG CAC TGC TGT CCT TCC TGC AGA AAC
        1683            1692            1701            1710            1719            1728
AGT TTC TCC TCC CCT CAG CCT TGT GGC CAG TTC CTC TTC ACA TGA AGC CCC
        1737            1746            1755            1764            1773            1782
TGG CAT TTG CTG GGG AAG GGA CTG GCC TGG TAC TTG CTG TTA GGG CAG GAA GGG
        1791            1800            1809            1818            1827            1836
GCA AAA GGA AGA CTT GGG TAG TAA TCT GGG GGT TCA GAT GGG TAG CAC TAA GCC
        1845            1854            1863            1872            1881            1890
AGC TGG CCT AAA GAT GCA ATA AGT TCC TAG GTA GTC TAC CCT TAC CTT GAG GAA
```

FIGURE 1E

```
      1899        1908        1917        1926        1935        1944
TGG GAA AAT GAA CCT CAG CCC ATT AGG CAG GAA AAG TTG ATA TTT AAT AAA CAA 1953        1962        1971
GGA AAG AGT GAA CTG AGA CCC CAA AAA AAA 3'
```

```
1    MNL---------------ALAGD--------------------------ILAAG--------  3536924
1    MTIFGGGQSKKAPLIGESGIPAYCLKTIGSRHILVAGGG                          gi1419440

14   ------QDAHCQLLRFQAHQQQGNKAEKAGSK-EQGPRQ                          3536924
41   ASKTGVLNEIQTHLFTTGSANQDVGFQSKCVGKFDTGSMA                         gi1419440

46   RKG--------------AAPAEKKCGA-----------------ETQ                  3536924
81   TMNMDVACAFDEISAKYVIAAGQENLCALYMTRAFKLNEE                         gi1419440

62   HEGLELRVENLQAVQTDF-SSDPLQKVVCFNHDN--TLLA                         3536924
121  NECLSFEIQKVSQVRSDFHASNSYQKCVRFDKSSRGKIFA                         gi1419440

99   TGGTDGYVRVWKVPSL-----------EKVLEFKAHEGEIEDL                      3536924
161  TGGADGHIRIWNAQIVFRAENEDAQPILTIQAHKADVDDI                         gi1419440

131  ALGPDGKLVTVGRDLKASVWQKDQLVTQLHWQENGPTFSS                         3536924
201  DFSKDSKTIISVGAEGAFIWSTQ-----------------                         gi1419440

171  TPYRYQACRFGQVPDQPAGLRLFTVQIPHKRLRQPPPCYL                         3536924
224  ------------------TGARLLDLQFPIEISR------                         gi1419440

211  TAWDGSNFLPLRTKSCGHEVVSCLDVSESGTFLGLGTVTG                         3536924
240  ------------------GFKSISSLAVSDCGNFTAVGTMSG                       gi1419440

251  SVAIYIAFSLQCLYYVREAHGIVVTDVAFLPEKGRG---                          3536924
264  SVLVFDTHECRRLYFSPESHGLFVTGIEFVSRTSPSICED                         gi1419440
```

```
5' GCT CTT CAC  CGC CGG CCT  CCC ACC CAG  CTC TCT GGT  CCC GGC AAG  ATG GCG
         9           18           27           36           45           54

GCT GCC GCG  GAG TGC GAT  GTG GTA ATG  GCG GCG ACC  GAG CCG CTC  GAC
                                     M     A   A   T    E   P   L    D
        63           72           81           90           99          108

GAC CAA GAG  GCG AAG GAA  GCA GAG ACT  TTC AAG GAA  CAA CCG GGC  AAG ATG GCG
    D   Q   E    A   K   E    A   E   T    F   K   E    Q   P   G    K   M   A
       117          126          135          144          153          162

TAT GCC AAG  AAA GAT TAC  AAT GAA GCT  TAT AAT TAT  TAT ACA GGA  AAT GCA TAC
    Y   A   K    K   D   Y    N   E   A    Y   N   Y    Y   T   G    N   A   Y
       171          180          189          198          207          216

ATG TGT CCT  AAA AAT AAT  GAA GCT AGC  TAT GGT AAT  TAT CGA GCA  GCC ATA GAT
    M   C   P    K   N   N    E   A   S    Y   G   N    Y   R   A    A   I   D
       225          234          243          252          261          270

CTT GGA AGG  TTC CGG GAA  GCT CTT GGA  GAT GCA CAG  CAG TCA GCC  ACC TTG ATG
    L   G   R    F   R   E    A   L   G    D   A   Q    Q   S   A    T   L   M
       279          288          297          306          315          324

GAC AGT TTT  GTC CGG GGA  CAT CTA CGA  GAG GGC AAG  TGC CAC CTC  TCT CTG GGG
    D   S   F    V   R   G    H   L   R    E   G   K    C   H   L    S   L   G
       333          342          351          360          369          378
```

FIGURE 4A

```
                              387  396  405  414  423  432
AAT GCC ATG GCA GCA TGT CGC AGC TTC CAG AGA GCC CTA GAA CTG GAT CAT AAA
 N   A   M   A   A   C   R   S   F   Q   R   A   L   E   L   D   H   K 441  450  459  468  477  486
AAT GCT CAG GCA CAA CAA GAG TTC AAG AAT GCT GCA GTC ATG GAA TAT GAG
 N   A   Q   A   Q   Q   E   F   K   N   A   A   V   M   E   Y   E 495  504  513  522  531  540
AAA ATA GCA GAA ACA GAT TTT GAG AAG CGA GAT TTT CGG AAG GTT GTT TTC TGC
 K   I   A   E   T   D   F   E   K   R   D   F   R   K   V   V   F   C 549  558  567  576  585  594
ATG CGT GCC CTA GAA TTT GCC CCT GCC CAT CGC TTC AAA ATC CTC AAG
 M   R   A   L   E   F   A   P   A   H   R   F   K   I   L   K 603  612  621  630  639  648
GCA TGT TTA GCA ATG CTG GGT CGT TAT CCA GAA GCA CAG TCT GTG GCT AGT
 A   C   L   A   M   L   G   R   Y   P   E   A   Q   S   V   A   S 657  666  675  684  693  702
GCA GAA TGT CTA CGA ATG GAT TCC ACC AAT GCA GAT CTG TAT GTA CGA GGT CTT
 A   E   C   L   R   M   D   S   T   N   A   D   L   Y   V   R   G   L

GAC ATT CTA CGA ATG GAT TCC ACC AAT GCA GAT CTG TAT GTA CGA GGT CTT
 D   I   L   R   M   D   S   T   N   A   D   L   Y   V   R   G   L
```

FIGURE 4B

| 711 | | | | 720 | | | | 729 | | | 738 | | 747 | | | 756 |
|---|---|---|---|---|---|---|---|---|---|---|---|---|---|---|---|---|
| TGC | CTT | TAT | TAC | GAA | GAT | TGT | ATT | GAG | AAG | GCA | GTT | CAG | TTT | GTA | CAG | GCT |
| C | L | Y | Y | E | D | C | I | E | K | A | V | Q | F | V | Q | A |

| 765 | | | | 774 | | | | 783 | | | 792 | | | | 801 | | 810 |
|---|---|---|---|---|---|---|---|---|---|---|---|---|---|---|---|---|---|
| CTC | AGG | ATG | GCT | CCT | GAC | CAC | GAG | AAG | GCC | TGC | ATT | GCC | TGC | AGA | AAT | GCC | AAA |
| L | R | M | A | P | D | H | E | K | A | C | I | A | C | R | N | A | K |

| 819 | | | | 828 | | | | 837 | | | | 846 | | | | 855 | 864 |
|---|---|---|---|---|---|---|---|---|---|---|---|---|---|---|---|---|---|
| GCA | CTC | AAA | GCA | AAG | GAA | AAG | GAT | GGG | AAT | AAA | GCA | TTT | AAG | GAA | GGA | AAT | TAC |
| A | L | K | A | K | E | K | D | G | N | K | A | F | K | E | G | N | Y |

| 873 | | | | 882 | | | | 891 | | | 900 | | | | 909 | | 918 |
|---|---|---|---|---|---|---|---|---|---|---|---|---|---|---|---|---|---|
| AAA | GCA | TAT | GAA | CTG | TAC | ACA | GAA | GCC | CTG | GGG | ATA | GAC | CCC | AAC | AAT | ATA | ATA |
| K | A | Y | E | L | Y | T | E | A | L | G | I | D | P | N | N | I | I |

| 927 | | | | 936 | | | | 945 | | | 954 | | | | 963 | | 972 |
|---|---|---|---|---|---|---|---|---|---|---|---|---|---|---|---|---|---|
| AAA | AAT | GCT | AAA | CTC | TAC | TGT | TAT | AAT | CGG | GGT | ACG | GTT | AAT | TCC | AAG | CTT | AGG |
| K | N | A | K | L | Y | C | Y | N | R | G | T | V | N | S | K | L | R |

| 981 | | | | 990 | | | | 999 | | | 1008 | | | | 1017 | | 1026 |
|---|---|---|---|---|---|---|---|---|---|---|---|---|---|---|---|---|---|
| AAA | CTA | GAT | GAT | GCA | ATA | GAA | GAC | TGC | ACA | AAT | GCA | GTG | AAG | CTT | GAT | GAC | ACT |
| K | L | D | D | A | I | E | D | C | T | N | A | V | K | L | D | D | T |

FIGURE 4C

```
          1035            1044            1053            1062           1071            1080
TAC ATA AAA GCC TAC TTG AGA AGA GCT CAG TGT TAC ATG GAC ACA GAA CAG TAT
 Y   I   K   A   Y   L   R   R   A   Q   C   Y   M   D   T   E   Q   Y 1089            1098            1107            1116           1125            1134
GAA GAA GCA CAG GTA CGA GAC TAT GAA AAA GTA TAC CAG ACA GAG AAA ACA GAA
 E   E   A   Q   V   R   D   Y   E   K   V   Y   Q   T   E   K   T   E 1143            1152            1161            1170           1179            1188
CAC AAA CAG CTC CTA AAA AAT GCG CAG CTG GAA CTG AAG AAG AGT AAG AGG AAA
 H   K   Q   L   L   K   N   A   Q   L   E   L   K   K   S   K   R   K 1197            1206            1215            1224           1233            1242
GAT TAC AAG ATT CTA GGA GAC GTG AAT GCC TCT GAG GAC GAG ATC AAG
 D   Y   K   I   L   G   D   V   N   A   S   E   D   E   I   K 1251            1260            1269            1278           1287            1296
AAA GCT TAT CGG AAA CGG GCC TTG ATG CAC CAT CCA GAT CGG CAT AGT GGA GCC
 K   A   Y   R   K   R   A   L   M   H   H   P   D   R   H   S   G   A 1305            1314            1323            1332           1341            1350
AGT GCT GAG GTT CAG AAG GAG AAG GAG AAG AAG TTC AAG GAA GTT GGA GAG GCC
 S   A   E   V   Q   K   E   K   E   K   K   F   K   E   V   G   E   A
```

FIGURE 4D

```
       1359            1368            1377            1386            1395            1404
TTT ACT ATC CTC TCT GAT CCC AAG AAA ACT CGC TAT GAC AGT GGA CAG GAC
 F   T   I   L   S   D   P   K   K   T   R   Y   D   S   G   Q   D 1413            1422            1431            1440            1449            1458
CTA GAT GAG GAG GGC ATG AAT ATG GGT GAT TTT GAT CCA AAC AAT ATC TTC AAG
 L   D   E   E   G   M   N   M   G   D   F   D   P   N   N   I   F   K 1467            1476            1485            1494            1503            1512
GCA TTC TTT GGC GGT CCT GGC GGC TTC AGC TTT GAA GCA TCT GGT CCA GGG AAT
 A   F   F   G   G   P   G   G   F   S   F   E   A   S   G   P   G   N 1521            1530            1539            1548            1557            1566
TTC TTT CAA TTT GGC TAA TGA AGG GCA ACC CAG AAC CCA GAA AAT GCA
 F   F   F   Q   F   G 1575            1584            1593            1602            1611            1620
GAT TCA CTC AGT TTA ATC TTG AAT GTG GAA ACA GTT CAC CTC CTC CCT TCA TCA 1629            1638            1647            1656            1665            1674
CGT CTC CGT GTG CTT AGA GCA GTT TCG TTT TCT CAG TTG GAT GCC CTG TGT CTC 1683            1692            1701            1710            1719            1728
TGT GAG TGG GGT GGA GCA AAG GGA ACC AAT GCC GAA GAC CGA CGG GGG CAG GGG AGG
```

FIGURE 4E

```
      1737       1746       1755       1764       1773       1782
GAG GCG GGG GTG GAC AGG GAG GCA GCT TGT GAA TTT TTG TTT TAC TGT TTA ACT
      1791       1800       1809
TTA TTA AAA AAG AAA AAA AAA AAG AGA GA 3'
```

FIGURE 4F

```
1   MAATEPE- - - - - - - - - - - LLDDQ- - - EAKREAETF              701698
1   MVAPGSVTSRLGSVFPFLLVLVDLQYEGAECGVNADVEKH                       gi468012

22  KEQGNAYYAKKDYNEAYNYYTKAIDMCPKNASYYGNRAAT                       701698
41  LELGKKLLAAGQLADALSQFHAAVDGDPDNYIAYYRRATV                       gi468012

62  LMMLGRFREALGDAQQSVRLDDSFVRGHLREGKCHLSLGN                       701698
81  FLAMGKSKAALPDLTKVIELKMDFTAARLQRGHLLLKQGK                       gi468012

102 AMAACRSFQRALEL- - DHKNAQAQQEFKNANAVMEYEKI                       701698
121 LDEAEDDFKKVLKSNPSENEEKEAQSQLVKSDEMQRLRSQ                       gi468012

139 AETDFEKRDFRKVVFCMDRALEFAPACHR- - FKILKAEC                       701698
161 ALDAFESSDFTAAITFLDKILE - - VCVWDAELRELRAEC                      gi468012

176 LAMLGRYPEAQSVASDILRMDSTNADALYVRGLCLYYE-D                       701698
198 FIKEGEPRKAISDLKASSKLKNDNTEAFYKIST-LYYELG                       gi468012

215 CIEKAVQFFVQALRMAPDHEKACIA-CRNAKALKAKKEDG                       701698
237 DHELSLSEVRECLKLDQDH-KRCFAHYKQVKKLNKLIESA                       gi468012

254 NKAFKEGNYKLAYELYTEALGIDPN - - -NIKTNAKLYCN                      701698
276 EELIKEGRYTDAISKYESVMKTEPGVHEYTIRSKERI-CH                       gi468012

290 RGTVNSKLRKLDDAIEDCTNAVKLDDTYIKAYLRRAQCYM                       701698
315 - - -CFSKDEKPVEAIRVCSEVLQVEPDNVNALKDRAEAYL                      gi468012
```

FIGURE 5A

```
330  DTEQYEEAVRDYEKVY-QTEKTKEHHKQLLKNAQLELKKSK      701698
352  IEEMYDEAIQDYETAQEHNENDQQIREGLEKAQRLLKQSQ       gi468012

369  RKDYYKILGVDKNASEDEIKKAYRKRALMHHPDRHSGASA       701698
392  RRDYYKILGVKRNAKKQEIKAYRKLALQWHPDNF--QNE        gi468012

409  EVQKEEEKKFKEVGEAFTILSDPKKKTRYDSGQD-LDEEG       701698
430  EKKKAEKKFIDIAAAKEVLSDPEMRKKFDDGEDPLDAES        gi468012

448  MNMGDFDPNNIFKAFFGGPGGFS-FEASGPGNFFFQFG         701698
470  QQGGGGNP---FHRSWNSWQGFSPFSGGPFRKFHFN          gi468012
```

FIGURE 5B

```
5' NTG ATT AGA CTC TCA AGC CTG TTG TGT TTT TGA TCT AGC CAT TTT CAA CCA         54

CTG TGG TGA ACA TTT AGC TCT GAA TAG GCT CAT CTT CAT ATG CAC ATT CTA         108

TTT GTA GAT GTT GCT ATG AGG ACA TCA GAT TCA TCA AAA ATG ACT GAC GTG GAG TCT  162
                          M   R   T   S   D   S   S   K   M   T   D   V   E   S

GGG GTC GCC AAT TTT GCA TCT TCA GCA AGG GCA CGC CGG AAT GCC TTA CCA         216
     G   V   A   N   F   A   S   S   A   R   G   R   R   N   A   L   P

GAC ATC CAG AGT TCA GCT GCC ACA GAC GGA ACC TCA GAT TTG CCC CTC AAA CTG     270
     D   I   Q   S   S   A   A   T   D   G   T   S   D   L   P   L   K   L

GAG GCT CTC TCC GTG AAG GAA GAT GCA AAA GAG AAA GAT GAA AAA ACA ACA CAA     324
     E   A   L   S   V   K   E   D   A   K   E   K   D   E   K   T   T   Q

GAG GCT CTC TCC GTG AAG CCT CAA AAT GAA GAA AAA ACA ATA ATC TAT CAA         378
     D   Q   L   E   K   P   Q   N   E   E   K

GAC CAA TTG GAA AAG CCT CAA AAT GAA GAA AAA ACA ATA ATC TAT CAA
     D   Q   L   E   K   P   Q   N   E   E   K
```

FIGURE 7A

```
        387                 396             405             414             423             432
GAG TGC TGA ATT TCT GCA TGT TGA AAG ACT TAG TGG TTC TGT TTT CTT GAG ACA 441                 450             459             468             477             486
TTT AAT CTG GTG RTA ACT GTG GTA ACA TTG CAG CCC TAA GCA GCA TGT GTA TAT 495                 504             513             522             531             540
TAG ATA ATT GTG TTG TGA TGC TAC TCA CTT TGA TTG CAA TGA TGT CCA AGG 549                 558             567             576             585             594
TAA GCT ATT AAA AGG CAG GTT ACT TCC AAA TCG CAC TGA AGG AAA AGG TTA AGA 603                 612             621             630             639             648
ATA ATA CAT GAT CAC AGA AAT GCA TAC CAC TGT CTG TAA ACC CAA CAA AAT TCA 657                 666             675             684             693             702
CTG TTC TCT TTT GGA TTT ATT TAG CCT GAT GTA TTT TTA ATT CAA TTT TTA TGG

711
TGA TGG GCA   3'
```

HUMAN PROTEIN KINASE AND KINASE INHIBITORS

FIELD OF THE INVENTION

This invention relates to nucleic acid and amino acid sequences of a human protein kinase and kinase inhibitors and to the use of these sequences in the diagnosis, prevention, and treatment of cell proliferation, and immune and developmental disorders.

BACKGROUND OF THE INVENTION

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate which drives activation is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

Protein tyrosine kinases, PTKs, specifically phosphorylate tyrosine residues on their target proteins and may be divided into transmembrane, receptor PTKs, and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include: epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Some of the receptors that function through non-receptor PTKs include those for cytokines and hormones (growth hormone and prolactin) and antigen-specific receptors on the surface of T and B lymphocytes. The protein products of oncogenes and many growth-factor receptors have protein kinase activities that phosphorylate tyrosine.

Another family of kinases is the protein kinase C (PKC) family. Phosphorylation plays an essential role in regulating PKC. These enzymes transduce signals promoting phospholipid hydrolysis and are recruited to membranes upon the production of diacylglycerol and, for the conventional isoforms, increased $Ca^{2+}$ concentrations. Binding of these cofactors results in conformational change that removes an autoinhibitory (pseudo substrate) domain from the active site, thus promoting substrate binding and phosphorylation. Apoptosis of prostate epithelial cells is regulated by activators and inhibitors of the PKC family. The PKC family of serine/threonine kinases has been associated with signal transduction regulation cell growth and differentiation but has recently been associated with the regulation of cell death (Day, M. L. et al. (1994) Cell Growth & Differ. 5: 735–741) (Powell, C. T. et al. (1996) Cell Growth & Differ. 7: 419–428). Most PKC isozymes require the physiological activator diacylglycerol, which is derived from membrane phospholipids. Additionally, PKC activity also requires association with cellular membranes and/or cytoskeletal components to execute many of its physiological functions. PKC modulates signal transduction pathways that have been linked to both positive and negative regulation of the cell cycle and the initiation of apoptosis. An example of a PKC which is involved in the growth-inhibitory action of transforming growth factor-beta1 (TGF-beta1) in PC3, a human prostate cancer cell line, is protein kinase K02B12 from *C. elegans*.

RNA-activated protein kinase (PKR) is a serine/threonine protein kinase induced by interferon treatment and activated by double stranded RNAs. When PKR becomes autophosphorylated, it catalyzes phosphorylation of the alpha subunit of protein synthesis eukaryotic initiation factor 2 (eLF-2). Protein kinase inhibitors (PKI) have demonstrated potential for their use in the treatment of human cancers, in particular leukemia. (Lock, R. B. (1997) Cancer Chemother. Pharmacol. 39(5): 399–409) An example of a serine/threonine kinase inhibitor is the P58 PKR inhibitor (PKRI) from *B. taurus*, a 504-amino acid hydrophilic protein. PKRI, expressed as a histidine fusion protein in *E. coli*, blocked both the autophosphorylation of PKR and phosphorylation of the alpha subunit of eLF-2. Western blot analysis showed that PKRI is present not only in bovine cells but also in human, monkey, and mouse cells, suggesting the protein is highly conserved. Another example of an inhibitor of protein kinase C is the protein kinase inhibitor from mouse, which acts as an inhibitor of cAMP-dependent protein kinase and protein kinase C.

The discovery of a new PK and PKI and the polynucleotides encoding them satisfies a need in the art by providing new compositions which are useful in the diagnosis, prevention, and treatment of diseases associated with cell proliferation, and in particular, cancer, immune responses, and development disorders.

SUMMARY OF THE INVENTION

The invention features a substantially purified human protein kinase (PK) comprising the amino acid sequence selected from the group consisting of SEQ ID NO:1.

The invention further provides a substantially purified variant of ABBR having at least 90% amino acid identity to the amino acid sequence of SEQ ID NO:1 or a fragment of SEQ ID NO:1. The invention also provides an isolated and purified polynucleotide sequence encoding the polypeptide comprising the amino acid sequence of SEQ ID NO:1 or a fragment of SEQ ID NO:1. The invention also includes an isolated and purified polynucleotide variant having at least 90% polynucleotide identity to the polynucleotide sequence encoding the polypeptide comprising the amino acid sequence of SEQ ID NO:1 or a fragment of SEQ ID NO:1.

Additionally, the invention provides a composition comprising a polynucleotide sequence encoding the polypeptide comprising the amino acid sequence of SEQ ID NO:1 or a fragment of SEQ ID NO:1. The invention further provides an isolated and purified polynucleotide sequence which hybridizes under stringent conditions to the polynucleotide sequence encoding the polypeptide comprising the amino acid sequence of SEQ ID NO:1 or a fragment of SEQ ID NO:1, as well as an isolated and purified polynucleotide sequence which is complementary to the polynucleotide sequence encoding the polypeptide comprising the amino acid sequence of SEQ ID NO:1 or a fragment of SEQ ID NO:1.

The invention also provides an isolated and purified polynucleotide sequence comprising SEQ ID NO:2 or a fragment of SEQ ID NO:2, and an isolated and purified polynucleotide variant having at least 90% polynucleotide identity to the polynucleotide sequence comprising SEQ ID NO:2 or a fragment of SEQ ID NO:2. The invention also provides an isolated and purified polynucleotide sequence which is complementary to the polynucleotide sequence comprising SEQ ID NO:2 or a fragment of SEQ ID NO:2.

The invention further provides an expression vector containing at least a fragment of the polynucleotide sequence encoding the polypeptide comprising the amino acid sequence of SEQ ID NO:1 or a fragment of SEQ ID NO:1. In another aspect, the expression vector is contained within a host cell.

The invention also provides a method for producing a polypeptide comprising the amino acid sequence of SEQ ID NO:1 or a fragment of SEQ ID NO:1, the method comprising the steps of: (a) culturing the host cell containing an expression vector containing at least a fragment of a polynucleotide sequence encoding PK under conditions suitable for the expression of the polypeptide; and (b) recovering the polypeptide from the host cell culture.

The invention also provides a pharmaceutical composition comprising a substantially purified PK having the amino acid sequence of SEQ ID NO:1 or a fragment of SEQ ID NO:1 in conjunction with a suitable pharmaceutical carrier.

The invention further includes a purified antibody which binds to a polypeptide comprising the amino acid sequence of SEQ ID NO:1 or a fragment of SEQ ID NO:1, as well as a purified agonist and a purified antagonist of the polypeptide.

The invention also provides a method for treating or preventing an immune response, the method comprising administering to a subject in need of such treatment an effective amount of an antagonist of PK.

The invention also provides a method for treating or preventing a cancer, the method comprising administering to a subject in need of such treatment an effective amount of an antagonist of PK.

The invention also provides a method for treating or preventing a developmental disorder, the method comprising administering to a subject in need of such treatment an effective amount of an antagonist of PK.

The invention also provides a method for detecting a polynucleotide encoding PK in a biological sample containing nucleic acids, the method comprising the steps of: (a) hybridizing the complement of the polynucleotide sequence encoding the polypeptide comprising SEQ ID NO:1 or a fragment of SEQ ID NO:1 to at least one of the nucleic acids of the biological sample, thereby forming a hybridization complex; and (b) detecting the hybridization complex, wherein the presence of the hybridization complex correlates with the presence of a polynucleotide encoding PK in the biological sample. In one aspect, the nucleic acids of the biological sample are amplified by the polymerase chain reaction prior to the hybridizing step.

The invention features substantially purified polypeptides, human protein kinase inhibitors, referred to collectively as "PKI" and individually as "PKI-1" and "PKI-2." In one aspect, the invention provides a substantially purified polypeptide, PKI, comprising an amino acid sequence selected from the group consisting of SEQ ID NO:4, SEQ ID NO:7, a fragment of SEQ ID NO:4, and a fragment of SEQ ID NO:7.

The invention further provides a substantially purified variant of PKI having at least 90% amino acid identity to the amino acid sequences of SEQ ID NO:4 or SEQ ID NO:7, or to a fragment of either of these sequences. The invention also provides an isolated and purified polynucleotide sequence encoding the polypeptide comprising an amino acid sequence selected from the group consisting of SEQ ID NO:4, SEQ ID NO:7, a fragment of SEQ ID NO:4, and a fragment of SEQ ID NO:7. The invention also includes an isolated and purified polynucleotide variant having at least 90% polynucleotide identity to the polynucleotide sequence encoding the polypeptide comprising an amino acid sequence selected from the group consisting of SEQ ID NO:4, SEQ ID NO:7, a fragment of SEQ ID NO:4, and a fragment of SEQ ID NO:7.

Additionally, the invention provides a composition comprising a polynucleotide sequence encoding the polypeptide comprising the amino acid sequence selected from the group consisting of SEQ ID NO:4, SEQ ID NO:7, a fragment of SEQ ID NO:4, and a fragment of SEQ ID NO:7. The invention further provides an isolated and purified polynucleotide sequence which hybridizes under stringent conditions to the polynucleotide sequence encoding the polypeptide comprising an amino acid sequence selected from the group consisting of SEQ ID NO:4, SEQ ID NO:7, a fragment of SEQ ID NO:4, and a fragment of SEQ ID NO:7, as well as an isolated and purified polynucleotide sequence which is complementary to the polynucleotide sequence encoding the polypeptide comprising the amino acid sequence selected from the group consisting of SEQ ID NO:4, SEQ ID NO:7, a fragment of SEQ ID NO:4, and a fragment of SEQ ID NO:7.

The invention also provides an isolated and purified polynucleotide sequence comprising a polynucleotide sequence selected from the group consisting of SEQ ID NO:5, SEQ ID NO:8, a fragment of SEQ ID NO:5, and a fragment of SEQ ID NO:8. The invention further provides an isolated and purified polynucleotide variant having at least 90% polynucleotide identity to the polynucleotide sequence comprising a polynucleotide sequence selected from the group consisting of SEQ ID NO:5, SEQ ID NO:8, a fragment of SEQ ID NO:5, and a fragment of SEQ ID NO:8, as well as an isolated and purified polynucleotide sequence which is complementary to the polynucleotide sequence comprising a polynucleotide sequence selected from the group consisting of SEQ ID NO:5, SEQ ID NO:8, a fragment of SEQ ID NO:5, and a fragment of SEQ ID NO:8.

The invention further provides an expression vector containing at least a fragment of the polynucleotide sequence encoding the polypeptide comprising an amino acid sequence selected from the group consisting of SEQ ID NO:4, SEQ ID NO:7, a fragment of SEQ ID NO:4, and a fragment of SEQ ID NO:7. In another aspect, the expression vector is contained within a host cell.

The invention also provides a method for producing a polypeptide comprising the amino acid sequence of SEQ ID NO:4, SEQ ID NO:7, a fragment of SEQ ID NO:4, or a fragment of SEQ ID NO:7, the method comprising the steps of: (a) culturing the host cell containing an expression vector containing at least a fragment of a polynucleotide sequence encoding ABBR under conditions suitable for the expression of the polypeptide; and (b) recovering the polypeptide from the host cell culture.

The invention also provides a pharmaceutical composition comprising a substantially purified ABBR having the amino acid sequence of SEQ ID NO:4, SEQ ID NO:7, a fragment of SEQ ID NO:4, or a fragment of SEQ ID NO:7 in conjunction with a suitable pharmaceutical carrier.

The invention further includes a purified antibody which binds to a polypeptide comprising the amino acid sequence of SEQ ID NO:4, SEQ ID NO:7, a fragment of SEQ ID NO:4, or a fragment of SEQ ID NO:7, as well as a purified agonist and a purified antagonist to the polypeptide. The invention also provides a method for treating or preventing an immune response, the method comprising administering to a subject in need of such treatment an effective amount of an antagonist of PKI.

The invention further includes a purified antibody which binds to a polypeptide comprising the amino acid sequence of SEQ ID NO:4, SEQ ID NO:7, a fragment of SEQ ID NO:4, or a fragment of SEQ ID NO:7, as well as a purified agonist and a purified antagonist to the polypeptide. The invention also provides a method for treating or preventing a cancer, the method comprising administering to a subject in need of such treatment an effective amount of an antagonist of PKI.

The invention further includes a purified antibody which binds to a polypeptide comprising the amino acid sequence of SEQ ID NO:4, SEQ ID NO:7, a fragment of SEQ ID NO:4, or a fragment of SEQ ID NO:7, as well as a purified agonist and a purified antagonist to the polypeptide. The invention also provides a method for treating or preventing a developmental disorder, the method comprising administering to a subject in need of such treatment an effective amount of an antagonist of PKI.

The invention also provides a method for detecting a polynucleotide encoding ABBR in a biological sample containing nucleic acids, the method comprising the steps of: (a) hybridizing the complement of the polynucleotide sequence encoding the polypeptide comprising SEQ ID NO:4, SEQ ID NO:7, a fragment of SEQ ID NO:4, or a fragment of SEQ ID NO:7 to at least one of the nucleic acids of the biological sample, thereby forming a hybridization complex; and (b) detecting the hybridization complex, wherein the presence of the hybridization complex correlates with the presence of a polynucleotide encoding PKI in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, 1D, 1E, and 1F show the amino acid sequence (SEQ ID NO:1) and nucleic acid sequence (SEQ ID NO:2) of protein kinase (PK). The alignment was produced using MACDNASIS software (Hitachi Software Engineering Co. Ltd. San Bruno, Calif.).

FIGS. 2A and 2B show the amino acid sequence alignments between PK (1762; SEQ ID NO:1) and a C. elegans protein kinase K02B12 (GI 1419440; SEQ ID NO:3) produced using the multisequence alignment program of DNASTAR software (DNASTAR Inc., Madison, Wis.).

FIGS. 4A, 4B, 4C, 4D, 4E, and 4F show the amino acid sequence (SEQ ID NO:4) and nucleic acid sequence (SEQ ID NO:5) of protein kinase inhibitor 1 (PKI-1). The alignment was produced using MACDNASIS PRO software (Hitachi Software Engineering Co. Ltd. San Bruno, Calif.).

FIGS. 5A and 5B show the amino acid sequence alignments between PKI-1 (701698; SEQ ID NO:4) and a Bos taurus PKR inhibitor P58 (GI 468012; SEQ ID NO:6) produced using the multisequence alignment program of DNASTAR software (DNASTAR Inc., Madison, Wis.).

FIGS. 7A and 7B show the amino acid sequence (SEQ ID NO:7) and nucleic acid sequence (SEQ ID NO:8) of protein kinase inhibitor 2 (PKI-2). The alignment was produced using MACDNASIS PRO software (Hitachi Software Engineering Co. Ltd. San Bruno, Calif.).

FIG. 8 shows the amino acid sequence alignments between PKI-2 (994480; SEQ ID NO:7) and mouse protein kinase inhibitor (GI 200497; SEQ ID NO:9) produced using the multisequence alignment program of DNASTAR software (DNASTAR Inc., Madison, Wis.).

DESCRIPTION OF THE INVENTION

Figure 3A:
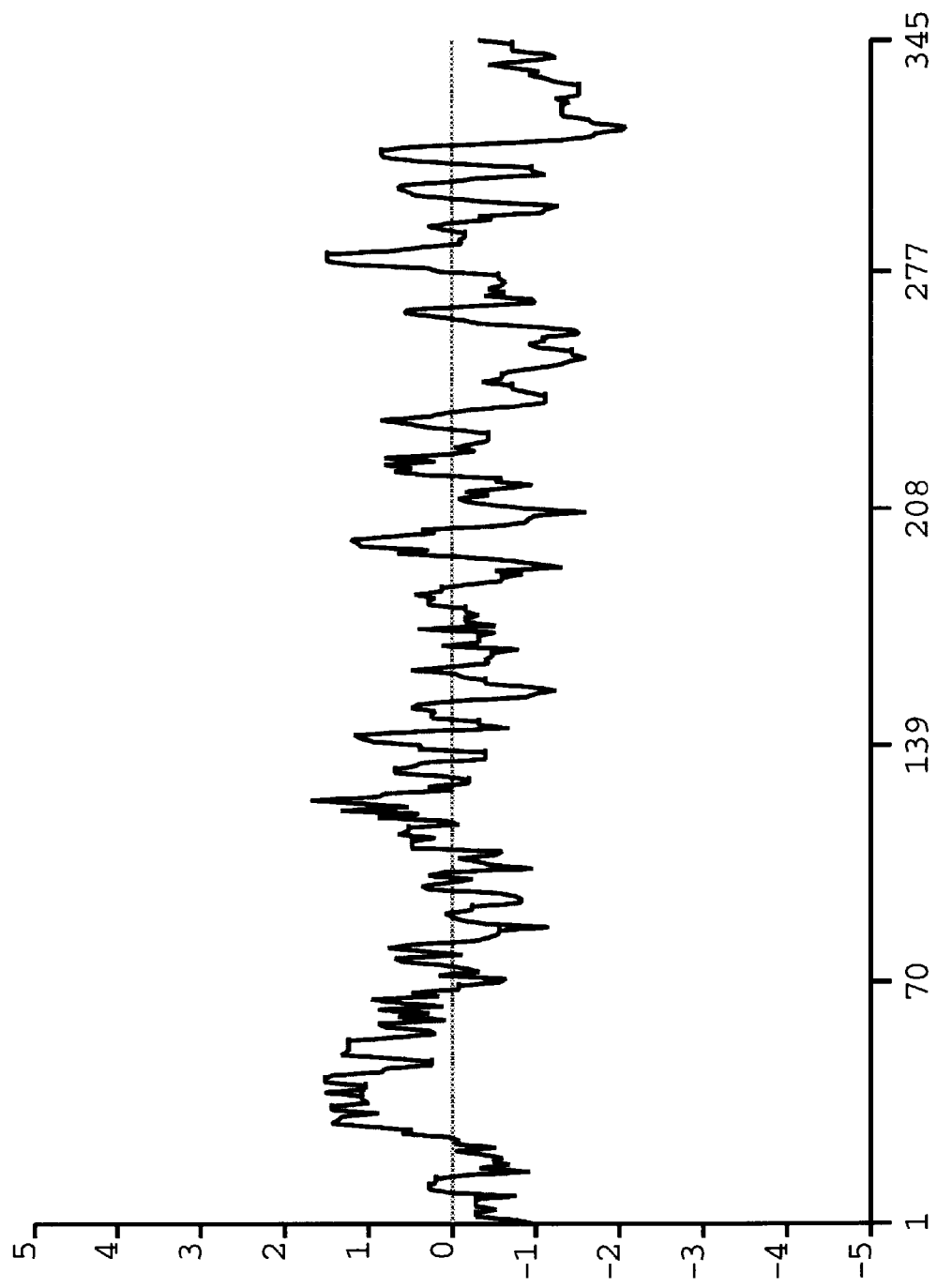
FIGS. 3A and 3B show the hydrophobicity plots for PK (SEQ ID NO:1) and protein kinase K02B12 (SEQ ID NO:3), respectively. The positive X axis reflects amino acid position, and the negative Y axis reflects hydrophobicity (MACDNASIS PRO software).
Figure 3B:
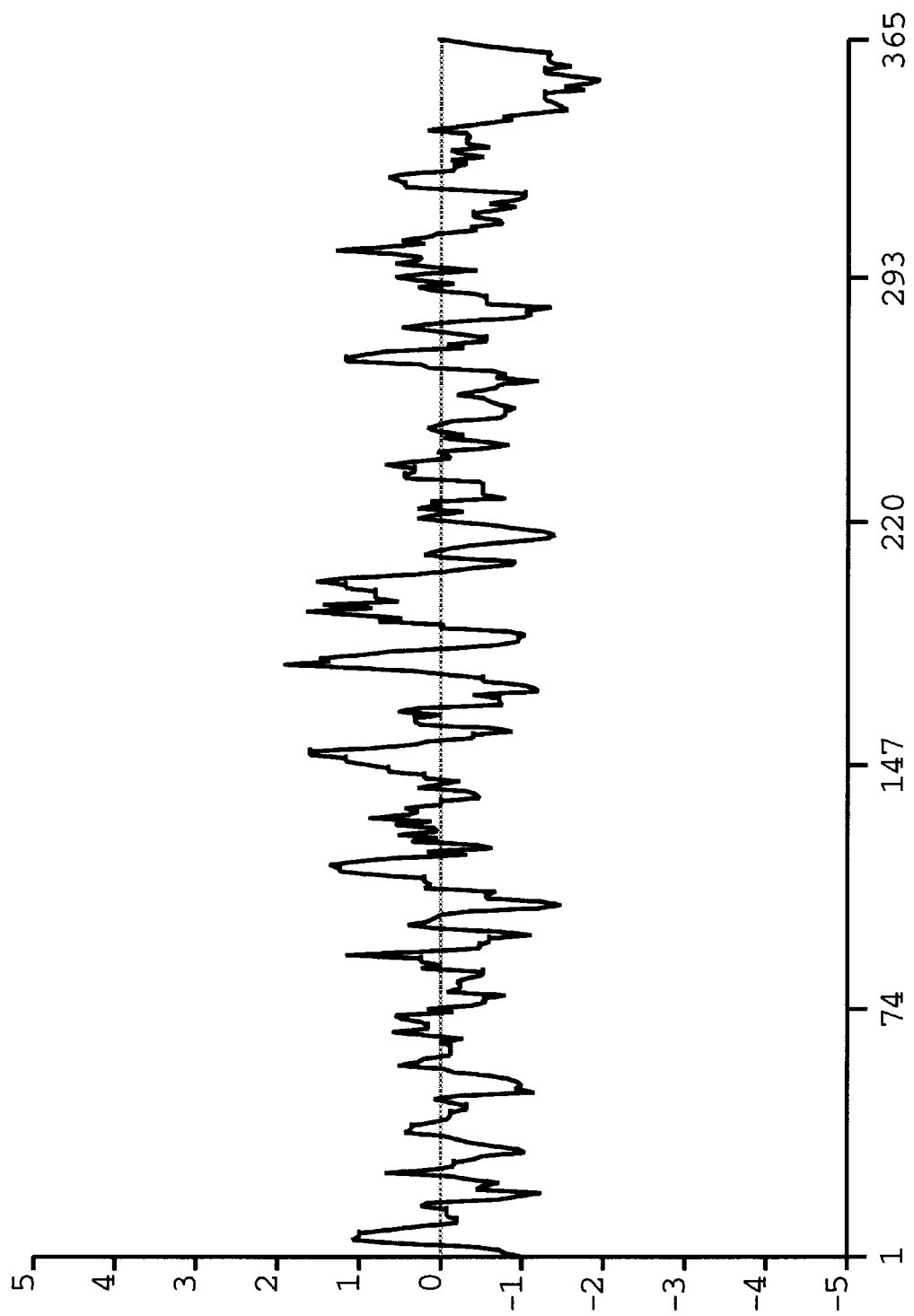
Figure 6A:
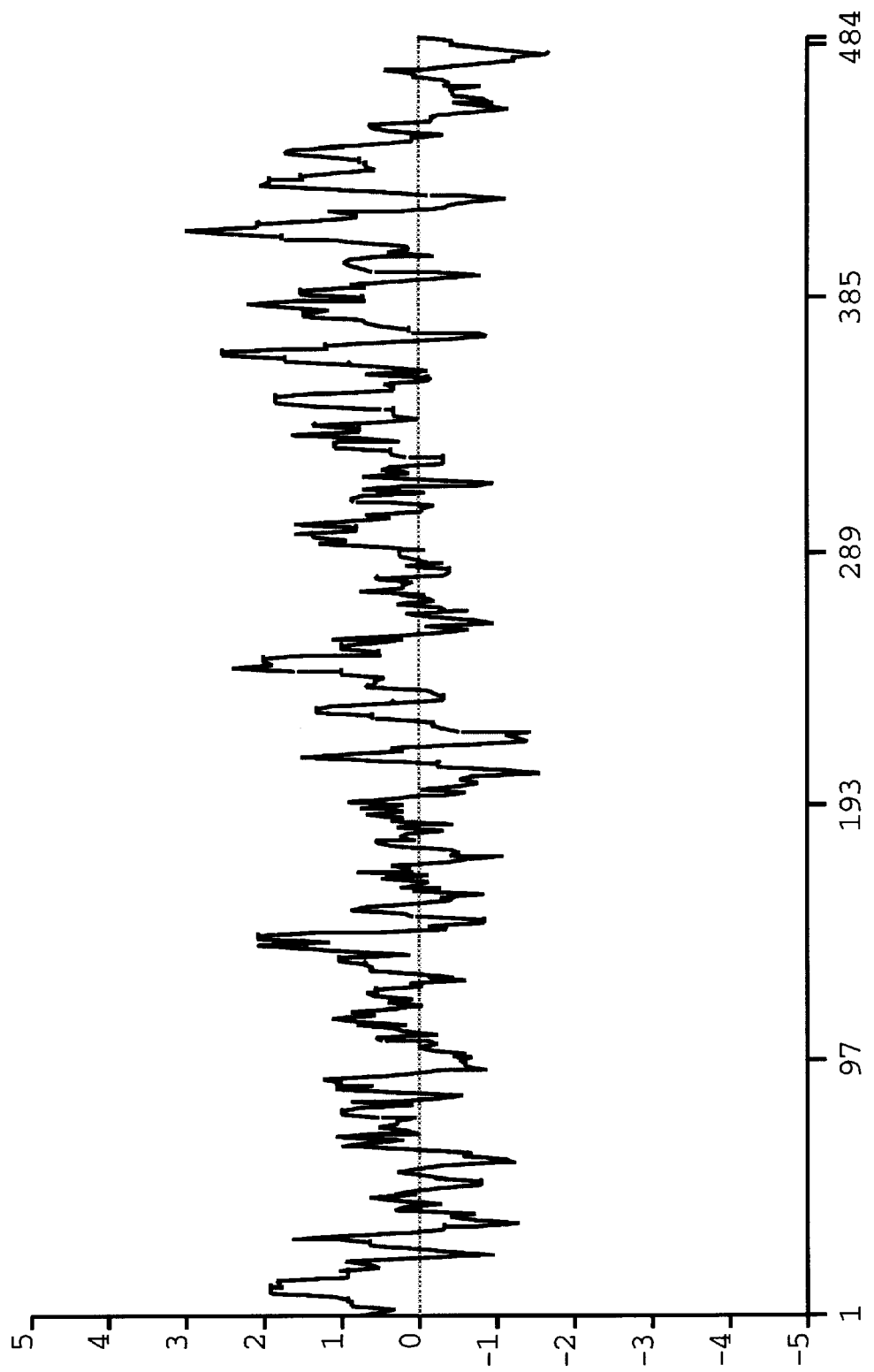
FIGS. 6A and 6B show the hydrophobicity plots for PKI-1 (SEQ ID NO:4) and PKR inhibitor P58 (SEQ ID NO:6), respectively. The positive X axis reflects amino acid position, and the negative Y axis reflects hydrophobicity (MACDNASIS PRO software).
Figure 6B:
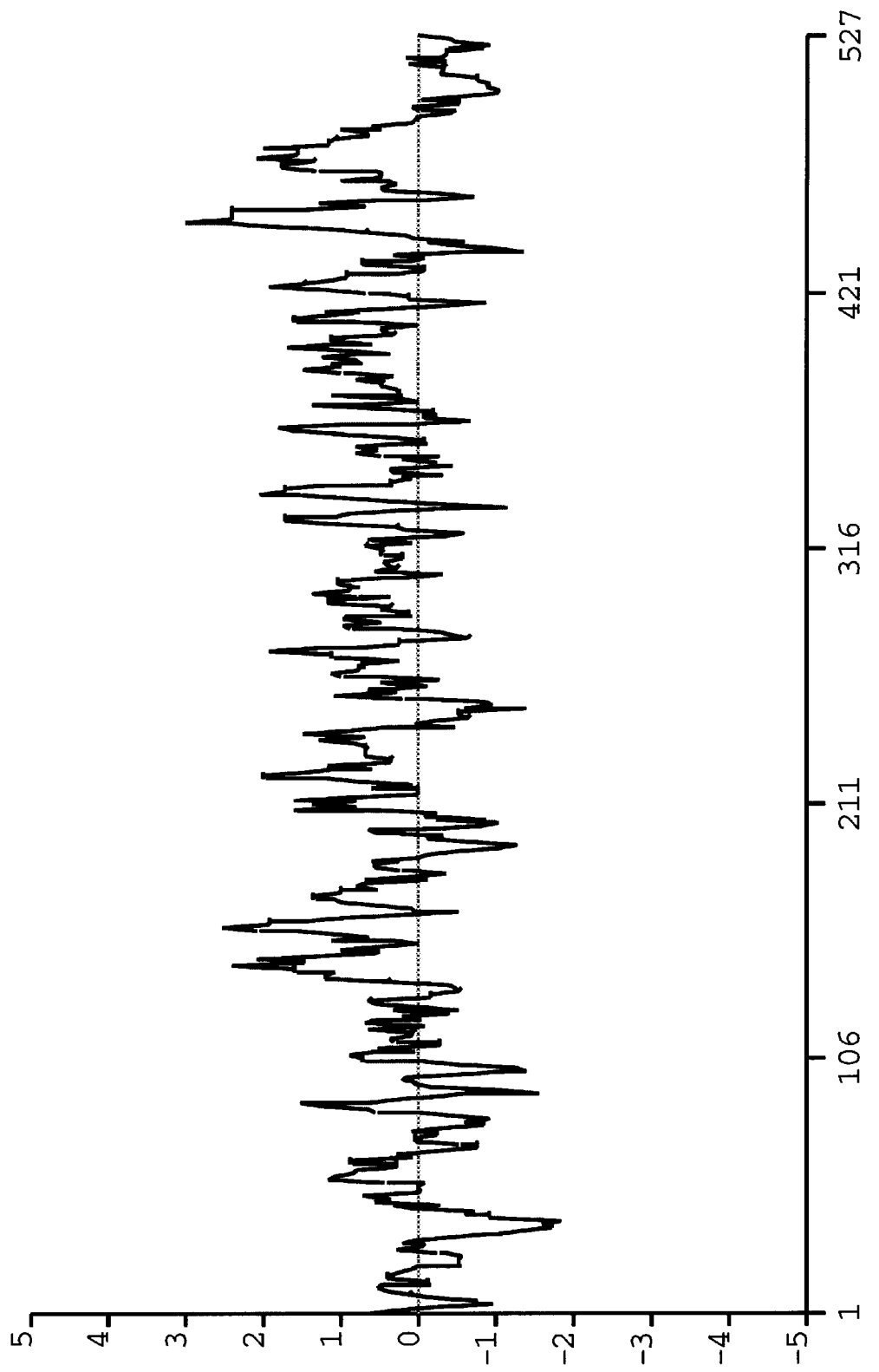
Figure 9A:
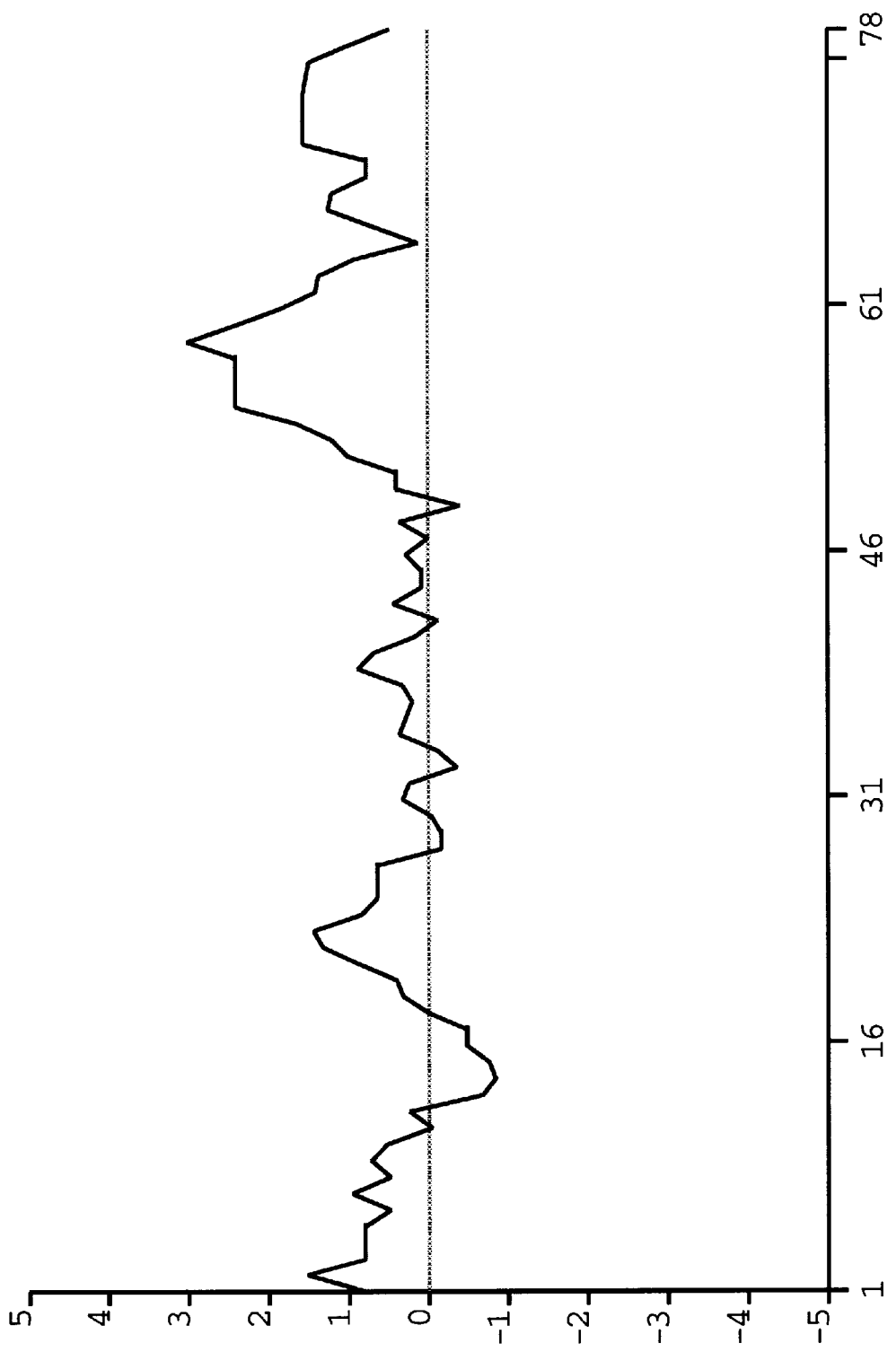
FIGS. 9A and 9B show the hydrophobicity plots for PKI-2 (SEQ ID NO:7) and mouse protein kinase inhibitor (SEQ ID NO:9), respectively. The positive X axis reflects amino acid position, and the negative Y axis reflects hydrophobicity (MACDNASIS PRO software).
Figure 9B:
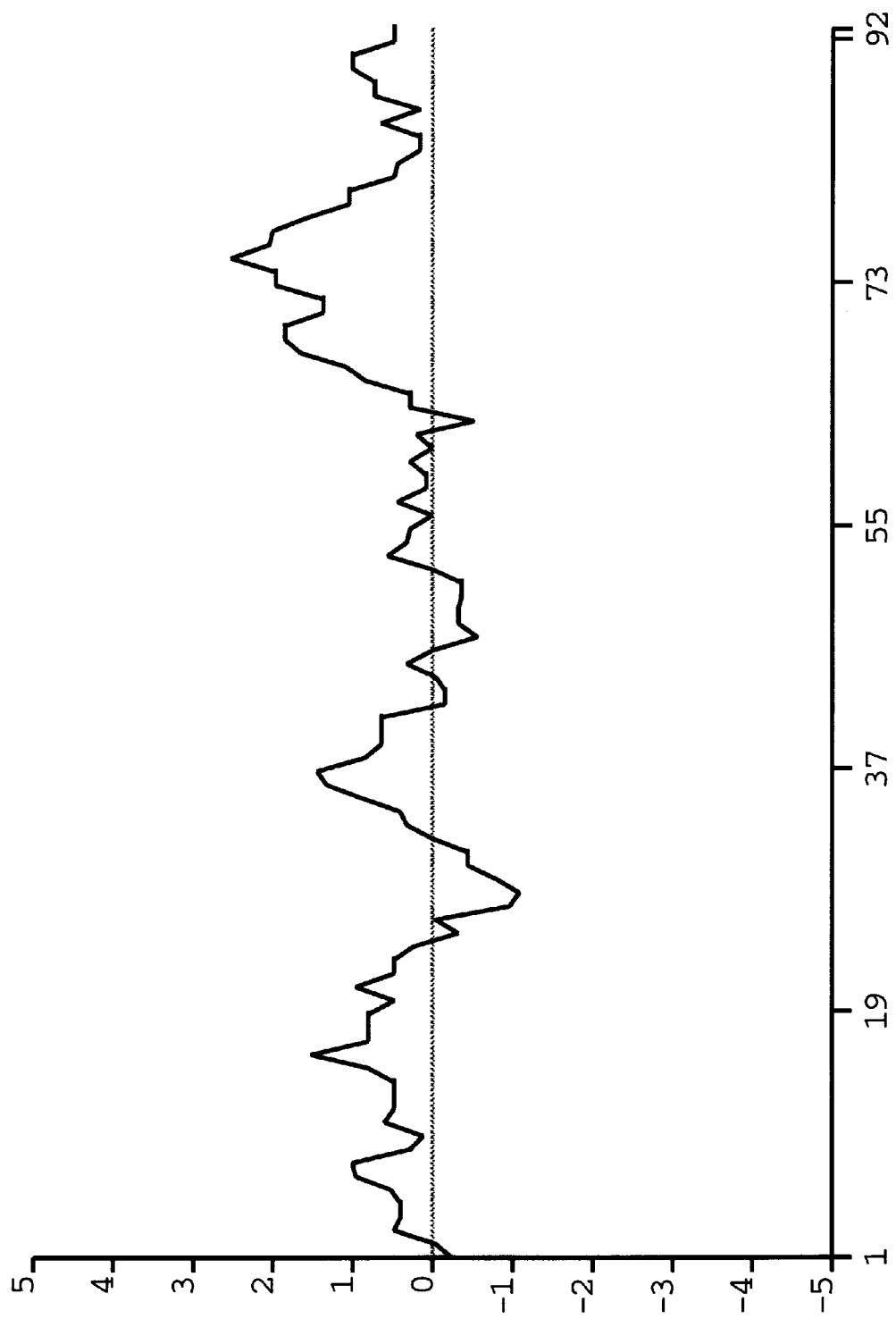

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

PK and PKI, as used herein, refers to the amino acid sequences of substantially purified PK and PKI obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to PK and PKI, increases or prolongs the duration of the effect of PK and PKI. Agonists may include proteins, nucleic acids, carbohydrates, or any other molecules which bind to and modulate the effect of PK and PKI.

An "allele" or "allelic sequence", as used herein, is an alternative form of the gene encoding PK and PKI. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence. "Altered" nucleic acid sequences encoding PK and PKI as used herein include those with deletions, insertions, or substitutions of different nucleotides resulting in a polynucleotide that encodes the same or a functionally equivalent PK and PKI. Included within this definition are polymorphisms which may or may not be readily detectable using a particular oligonucleotide probe of the polynucleotide encoding PK and PKI, and unexpected hybridization to alleles, with a locus other than the normal chromosomal locus for the polynucleotide sequence encoding PK and PKI. The encoded protein may also be "altered" and contain deletions, insertions, or substitutions of amino acid residues which produce a silent change and result in a functionally equivalent PK and PKI. Deliberate amino acid substitutions may be made on the basis of similarity in polarity, charge, solubility, hydrophobicity, hydrophilicity, and/or the amphipathic nature of the residues as long as the biological or immunological activity of PK and PKI is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine. "Amino acid sequence" as used herein refers to an oligopeptide, peptide, polypeptide, or protein sequence, and fragment thereof, and to naturally occurring or synthetic molecules. Fragments of PK and PKI are preferably about 5 to about 15 amino acids in length and retain the biological activity or the immunological activity of PK and PKI. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual,* Cold Spring Harbor Press, Plainview, N.Y.).

The term "antagonist" as used herein, refers to a molecule which, when bound to PK and PKI, decreases the amount or the duration of the effect of the biological or immunological activity of PK and PKI. Antagonists may include proteins, nucleic acids, carbohydrates, antibodies or any other molecules which decrease the effect of PK and PKI.

As used herein, the term "antibody" refers to intact molecules as well as fragments thereof, such as Fab, F(ab')$_2$, and Fv, which are capable of binding the epitopic determinant. Antibodies that bind PK and PKI polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic PK and PKI, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding PK and PKI or fragments thereof may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW fragment assembly system, GCG, Madison, Wis.). Some sequences have been both extended and assembled to produce the consensus sequence.

The term "correlates with expression of a polynucleotide", as used herein, indicates that the detection of the presence of ribonucleic acid by northern analysis is indicative of the presence of mRNA encoding PK and PKI in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to PK and PKI or the encoded PK and PKI. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15: 345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of PK and PKI. For example, modulation may cause an increase or a decrease in protein activity, binding characteristics, or any other biological, functional or immunological properties of PK and PKI.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8: 53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence" which encompasses full-length PK and PKI and fragments thereof.

The term "sample", as used herein, is used in its broadest sense. A biological sample suspected of containing nucleic acid encoding PK and PKI, or fragments thereof, or PK and PKI itself may comprise a bodily fluid, extract from a cell, chromosome, organelle, or membrane isolated from a cell, a cell, genomic DNA, RNA, or cDNA (in solution or bound to a solid support, a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5X SSPE, 0.3% SDS, and 200 μg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of PK and PKI, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of new two new human protein kinase inhibitors (hereinafter individually referred to as PKI-1 and PKI-2 and collectively, as PKI) and one protein kinase (PK), the polynucleotides encoding PKI and PK, and the use of these compositions for the diagnosis, prevention, or treatment of neoplastic, immune, developmental, and neuronal disorders.

Nucleic acids encoding PK of the present invention were first identified in Incyte Clone 3536924 from the KIDN-NOT25 cDNA library using a computer search for amino acid sequence alignments. A consensus sequence, SEQ ID NO:2, was derived from the extension and assembly of Incyte Clones 3536924 (KIDNNOT25), 840078 (PROSTUT05), 1905151 (OVARNOT07), 1966854 (BRSTNOT04), 860323 (BRAITUT03), 1975789 (PANCTUT02), and 1316003 (BLADTUT02).

In one embodiment, the invention encompasses a polypeptide comprising the amino acid sequence of SEQ ID NO:1, as shown in FIGS. 1A, 1B, 1C, 1D, and 1E. PK is 345 amino acids in length and has three potential casein kinase II phosphorylation sites at residues $T^{60}$, $T^{211}$, and $S^{232}$; and one protein kinase C phosphorylation sites at residue $S^{313}$. As shown in FIGS. 2A and 2B, PK has chemical and structural homology with protein kinase K02B12 (GI 1419440). In particular, PK and the protein kinase K02B12 share 15% sequence identity. Northern analysis of PK shows expression in various cDNA libraries, 60% of the which are associated with cancer, 26% of which are associated with immune response, and 16% of which are associated with development.

Nucleic acids encoding PKI-1 of the present invention were first identified in Incyte Clone 701698 from the SYN-ORAT03 cDNA library using a computer search for amino acid sequence alignments. A consensus sequence, SEQ ID NO:5, was derived from the extension and assembly of Incyte Clones 701698 (SYNORAT03), 1819989 (GBLATUTO), 827908 (PROSNOT06), 152283 (BLADTUT04), and 1296910 (BRSTNOT07).

In one embodiment, the invention encompasses a polypeptide comprising the amino acid sequence of SEQ ID NO:4, as shown in FIGS. 4A, 4B, 4C, 4D, 4E, and 1F. PKI-1 is 484 amino acids in length and has a potential cAMP- and cGMP-dependent protein kinase phosphorylation site at residue $T^{435}$; seven potential casein kinase II phosphorylation sites at residues $T^4$, $T^{20}$, $T^{141}$, $T^{198}$, $S^{383}$, $T^{435}$, and $S^{439}$; one potential glycosaminoglycan attachment site at residue $S^{474}$; four potential protein kinase C phosphorylation sites at residues $T^{20}$, $S^{78}$, $T^{347}$, and $S^{367}$; two potential tyrosine kinase phosphorylation sites at residues $K^{32}$, $K^{255}$, and $R^{339}$; and one potential prokaryotic membrane lipoprotein lipid attachment site at residue $H^{96}$. As shown in FIGS. 5A and 5B, PKI-1 has chemical and structural homology with PKR inhibitor P58 from *B. taurus* protein (GI 468012). In particular, PKI-1 and the PKR inhibitor P58 protein share 25% sequence identity. Northern analysis of PKI-1 shows expression in various cDNA libraries, 47% of the which are associated with cancer, 25% of which are associated with immune response, and 18% of which are associated with development.

Nucleic acids encoding PKI-2 of the present invention were first identified in Incyte Clone 994480 from the COLN-NOT11 cDNA library using a computer search for amino acid sequence alignments. A consensus sequence, SEQ ID NO:8, was derived from the extension and assembly of Incyte Clone: 994480 (COLNNOT11).

Figure 8:
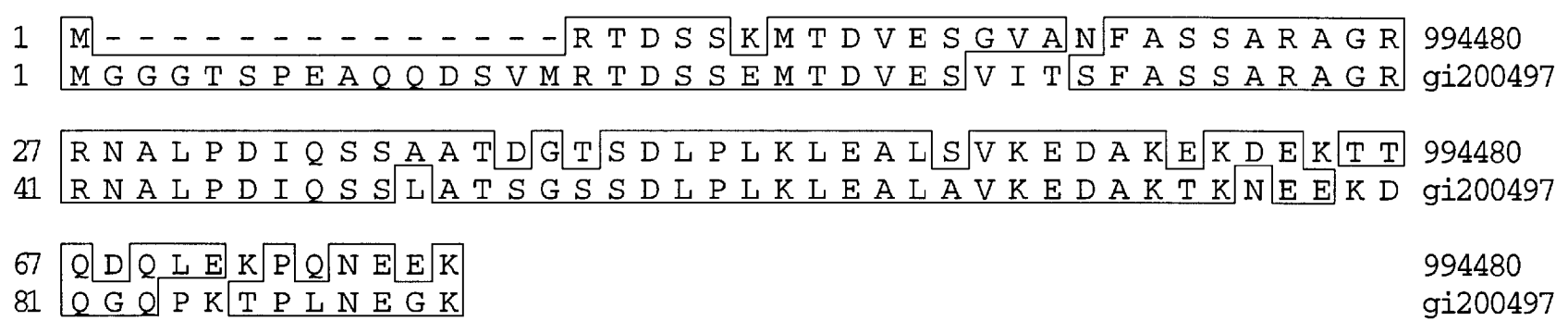

In one embodiment, the invention encompasses a polypeptide comprising the amino acid sequence of SEQ ID NO:7, as shown in FIGS. 7A and 7B. PKI-2 is 78 amino acids in length and has three potential casein kinase II phosphorylation sites at residues $T^9$, $S^{53}$, and $T^{65}$; and three potential protein kinase C phosphorylation sites at residues $S^5$, $S^{21}$, and $S^{53}$. As shown in FIG. 8, PKI-2 has chemical and structural homology with a mouse protein kinase inhibitor (GI 200496). In particular, PKI-2 and the mouse protein kinase inhibitor protein share 74% sequence identity. Northern analysis of PKI-2 shows expression in various cDNA libraries; 53% of which are associated with cancers; 16% of the which are associated with immune response, and 16% of which are associated with development.

The invention also encompasses PK and PKI variants. A preferred PK and PKI variant is one having at least about 80%, more preferably at least about 90%, and most preferably at least about 95% amino acid sequence identity to the PK and PKI amino acid sequence.

The invention also encompasses polynucleotides which encode PK and PKI. In a particular embodiment, the invention encompasses a polynucleotide sequence comprising the sequence of SEQ ID NO:2, which encodes a PK. In a further embodiment, the invention encompasses the polynucleotide sequence comprising the sequence of SEQ ID NO:4, and SEQ ID NO:7 as shown in FIGS. 4A, 4B, 4C, 4D, 4E, and 4F, and FIGS. 7A and 7B.

The invention also encompasses a variant of a polynucleotide sequence encoding PK. In particular, such a variant polynucleotide sequence will have at least about 80%, more preferably at least about 90%, and most preferably at least about 95% polynucleotide sequence identity to the polynucleotide sequence encoding PK. A particular aspect of the invention encompasses a variant of SEQ ID NO:2 which has at least about 80%, more preferably at least about 90%, and most preferably at least about 95% polynucleotide sequence identity to SEQ ID NO:2. The invention further encompasses a polynucleotide variant of SEQ ID NO:4 and DEQ ID NO:7 having at least about 80%.

The invention also encompasses polynucleotides which encode PK and PKI. Accordingly, any nucleic acid sequence which encodes the amino acid sequence of PK and PKI can be used to produce recombinant molecules which express PK and PKI. In a particular embodiment, the invention encompasses the polynucleotides comprising the nucleic acid sequences of SEQ ID NO:2, SEQ ID NO4, and SEQ ID NO8, as shown in FIGS. 1A, 1B, 1C, 1D, and 1E, and FIGS. 7A AND 7B, respectively.

It will be appreciated by those skilled in the art that as a result of the degeneracy of the genetic code, a multitude of nucleotide sequences encoding PK and PKI, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring PK and PKI, and all such variations are to be considered as being specifically disclosed.

Although nucleotide sequences which encode PK and PKI and its variants are preferably capable of hybridizing to the nucleotide sequence of the naturally occurring PK and PKI under appropriately selected conditions of stringency, it may be advantageous to produce nucleotide sequences encoding PK and PKI or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding PK and PKI and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode PK and PKI and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding PK and PKI or any fragment thereof.

Also encompassed by the invention are polynucleotide sequences that are capable of hybridizing to the claimed nucleotide sequences, and in particular, those shown in SEQ ID NOs:2 and 4, under various conditions of stringency as taught in Wahl, G. M. and S. L. Berger (1987; Methods Enzymol. 152: 399–407) and Kimmel, A. R. (1987; Methods Enzymol. 152: 507–511).

Methods for DNA sequencing which are well known and generally available in the art and may be used to practice any of the embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE with amplication system marketed by GIBCO/BRL (Gaithersburg, Md.). Preferably, the process is automated with machines such as the MICROLAB 2200 (Hamilton, Reno, Nev.), Peltier thermal cycler (PTC200; MJ Research, Watertown, Mass.) and the ABI Catalyst and 373 and 377 DNA sequencers (Perkin Elmer).

The nucleic acid sequences encoding PK and PKI may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2: 318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16: 8186). The primers may be designed using commercially available software such as OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1: 111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19: 3055–3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. GENOTYPER and SEQUENACE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode PK and PKI may be used in recombinant DNA molecules to direct expression of PK and PKI, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express PK and PKI.

As will be understood by those of skill in the art, it may be advantageous to produce PKI-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter PK and PKI encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding PK and PKI may be ligated to a heterologous sequence to encode a fusion protein. For example, to screen peptide libraries for inhibitors of PK and PKI activity, it may be useful to encode a chimeric PK and PKI protein that can be recognized by a commercially available antibody. A fusion protein may also be engineered to contain a cleavage site located between the PK and PKI encoding sequence and the heterologous protein sequence, so that PK and PKI may be cleaved and purified away from the heterologous moiety.

In another embodiment, sequences encoding PK and PKI may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of PK and PKI, or a fragment thereof. For example, peptide synthesis can be performed using various solid-phase techniques (Roberge, J. Y. et al. (1995) Science 269: 202–204) and automated synthesis may be achieved, for example, using the ABI 431A peptide synthesizer (Perkin Elmer).

The newly synthesized peptide may be substantially purified by preparative high performance liquid chromatography (e.g., Creighton, T. (1983) *Proteins, Structures and Molecular Principles,* WH Freeman and Co., New York, N.Y.). The composition of the synthetic peptides may be confirmed by amino acid analysis or sequencing (e.g., the Edman degradation procedure; Creighton, supra). Additionally, the amino acid sequence of PK and PKI, or any part thereof, may be altered during direct synthesis and/or combined using chemical methods with sequences from other proteins, or any part thereof, to produce a variant polypeptide.

In order to express a biologically active PK and PKI, the nucleotide sequences encoding PK and PKI or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding PK and PKI and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual,* Cold Spring Harbor Press, Plainview, N.Y., and Ausubel, F. M. et al. (1989) *Current Protocols in Molecular Biology,* John Wiley & Sons, New York, N.Y.

A variety of expression vector/host systems may be utilized to contain and express sequences encoding PK and PKI. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (GIBCO/BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding PK and PKI, vectors based on SV40 or EBV may be used with an appropriate selectable marker.

In bacterial systems, a number of expression vectors may be selected depending upon the use intended for PK and PKI. For example, when large quantities of PK and PKI are needed for the induction of antibodies, vectors which direct high level expression of fusion proteins that are readily purified may be used. Such vectors include, but are not limited to, the multifunctional $E.$ $coli$ cloning and expression vectors such as BLUESCRIPT (Stratagene), in which the sequence encoding PK and PKI may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264: 5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, $Saccharomyces$ $cerevisiae,$ a number of vectors containing constitutive or inducible promoters such as alpha factor, alcohol oxidase, and PGH may be used. For reviews, see Ausubel et al. (supra) and Grant et al. (1987) Methods Enzymol. 153: 516–544.

In cases where plant expression vectors are used, the expression of sequences encoding PK and PKI may be driven by any of a number of promoters. For example, viral promoters such as the 35S and 19S promoters of CaMV may be used alone or in combination with the omega leader sequence from TMV (Takamatsu, N. (1987) EMBO J. 6: 307–311). Alternatively, plant promoters such as the small subunit of RUBISCO or heat shock promoters may be used (Coruzzi, G. et al. (1984) EMBO J. 3: 1671–1680; Broglie, R. et al. (1984) Science 224: 838–843; and Winter, J. et al. (1991) Results Probl. Cell Differ. 17: 85–105). These constructs can be introduced into plant cells by direct DNA transformation or pathogen-mediated transfection. Such techniques are described in a number of generally available reviews (see, for example, Hobbs, S. or Murry, L. E. in McGraw Hill $Yearbook$ $of$ $Science$ $and$ $Technology$ (1992) McGraw Hill, New York, N.Y.; pp. 191–196).

An insect system may also be used to express PK and PKI. For example, in one such system, $Autographa$ $californica$ nuclear polyhedrosis virus (AcNPV) is used as a vector to express foreign genes in $Spodoptera$ $frugiperda$ cells or in Trichoplusia larvae. The sequences encoding PK and PKI may be cloned into a non-essential region of the virus, such as the polyhedrin gene, and placed under control of the polyhedrin promoter. Successful insertion of PK and PKI will render the polyhedrin gene inactive and produce recombinant virus lacking coat protein. The recombinant viruses may then be used to infect, for example, $S.$ $frugiperda$ cells or Trichoplusia larvae in which PK and PKI may be expressed (Engelhard, E. K. et al. (1994) Proc. Nat. Acad. Sci. 91: 3224–3227).

In mammalian host cells, a number of viral-based expression systems may be utilized. In cases where an adenovirus is used as an expression vector, sequences encoding PK and PKI may be ligated into an adenovirus transcription/translation complex consisting of the late promoter and tripartite leader sequence. Insertion in a non-essential E1 or E3 region of the viral genome may be used to obtain a viable virus which is capable of expressing PK and PKI in infected host cells (Logan, J. and Shenk, T. (1984) Proc. Natl. Acad. Sci. 81: 3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding PK and PKI. Such signals include the ATG initiation codon and adjacent sequences. In cases where sequences encoding PK and PKI, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20: 125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express PK and PKI may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11: 223–32) and adenine phosphoribosyltransferase (Lowy, I. et al. (1980) Cell 22: 817–23) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77: 3567–70); npt, which confers resistance to the aminoglycosides neomycin and G-418 (Colbere-Garapin, F. et al (1981) J. Mol. Biol. 150: 1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85: 8047–51). Recently, the use of visible markers has gained popularity with such markers as anthocyanins, βglucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55: 121–131).

Although the presence/absence of marker gene expression suggests that the gene of interest is also present, its presence and expression may need to be confirmed. For example, if the sequence encoding PK and PKI is inserted within a marker gene sequence, transformed cells containing sequences encoding PK and PKI can be identified by the absence of marker gene function. Alternatively, a marker gene can be placed in tandem with a sequence encoding PK and PKI under the control of a single promoter. Expression of the marker gene in response to induction or selection usually indicates expression of the tandem gene as well.

Alternatively, host cells which contain the nucleic acid sequence encoding PK and PKI and express PK and PKI may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of nucleic acid or protein.

The presence of polynucleotide sequences encoding PK and PKI can be detected by DNA—DNA or DNA-RNA hybridization or amplification using probes or fragments or fragments of polynucleotides encoding PK and PKI. Nucleic acid amplification based assays involve the use of oligonucleotides or oligomers based on the sequences encoding PK and PKI to detect transformants containing DNA or RNA encoding PK and PKI.

A variety of protocols for detecting and measuring the expression of PK and PKI, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on PK and PKI is preferred, but a competitive binding assay may be employed. These and other assays are described, among other places, in Hampton, R. et al. (1990; *Serological Methods, a Laboratory Manual,* APS Press, St Paul, Minn.) and Maddox, D. E. et al. (1983; J. Exp. Med. 158: 1211–1216).

A wide variety of labels and conjugation techniques are known by those skilled in the art and may be used in various nucleic acid and amino acid assays. Means for producing labeled hybridization or PCR probes for detecting sequences related to polynucleotides 30 encoding PK and PKI include oligolabeling, nick translation, end-labeling or PCR amplification using a labeled nucleotide. Alternatively, the sequences encoding PK and PKI, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP. and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding PK and PKI may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode PK and PKI may be designed to contain signal sequences which direct secretion of PK and PKI through a prokaryotic or eukaryotic cell membrane. Other constructions may be used to join sequences encoding PK and PKI to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and PK and PKI may be used to facilitate purification. One such expression vector provides for expression of a fusion protein containing PK and PKI and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3: 263–281) while the enterokinase cleavage site provides a means for purifying PK and PKI from the fusion protein. A discussion of vectors which contain fusion proteins is provided in Kroll, D. J. et al. (1993; DNA Cell Biol. 12: 441–453).

In addition to recombinant production, fragments of PK and PKI may be produced by direct peptide synthesis using solid-phase techniques (Merrifield J. (1963) J. Am. Chem.

Soc. 85: 2149–2154). Protein synthesis may be performed using manual techniques or by automation. Automated synthesis may be achieved, for example, using an Applied Biosystems 431 A peptide synthesizer (Perkin Elmer). Various fragments of PK and PKI may be chemically synthesized separately and combined using chemical methods to produce the full length molecule.

Therapeutics

Chemical and structural homology exists between PK and the protein sequences of protein kinase K02B12 (GI 1419440; SEQ ID NO:3). Northern analysis shows that the expression of PK (SEQ ID NO:1) is associated with cancer, immune response, and development.

Therefore, in one embodiment, an antagonist of PK or a fragment or derivative thereof may be administered to a subject to treat or prevent a cancer. Such cancers include, but are not limited to, adenocarcinoma, leukemia, lymphoma, melanoma, myeloma, sarcoma, and teratocarcinoma; and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds PK may be used directly as an antagonist or indirectly as a targeting or delivery mechanism for bringing a pharmaceutical agent to cells or tissues which express PK.

In another embodiment, an antagonist of PK may be administered to a subject to prevent or treat an immune disorder. Such disorders may include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma.

In another embodiment, an antagonist of PK may be administered to a subject to prevent or treat a developmental disorder. Such disorders include, but are not limited to, renal tubular acidosis, Cushing's syndrome, achondroplastic dwarfism, Duchenne and Becker muscular dystrophy, gonadal dysgenesis, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spinal bifida, and congenital glaucoma, cataract, or sensorineural hearing loss.

In another embodiment, a vector expressing the complement of the polynucleotide encoding PK may be administered to a subject to treat or prevent a cancer including, but not limited to, those described above.

In another embodiment, a vector expressing the complement of the polynucleotide encoding PK may be administered to a subject to treat or prevent an immune disorder including, but not limited to, those described above.

In another embodiment, a vector expressing the complement of the polynucleotide encoding PK may be administered to a subject to treat or prevent developmental disorder including, but not limited to, the those described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of PK may be produced using methods which are generally known in the art. In particular, purified PK may be used to produce antibodies or to screen libraries of pharmaceutical agents to identify those which specifically bind PK.

Antibodies to PK may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with PK or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

Chemical and structural homology exists between PKI-1 and the protein sequences of PKR inhibitor p58, and between PKI-2 and mouse protein kinase inhibitor. Northern analysis shows that the expression of both PKI-1 and PKI-2 is associated with cancer, immune response, and development. Therapeutic uses for both PKI-1 and PKI-2 (PKI) are described collectively below.

In one embodiment, an antagonist of PKI or a fragment or derivative of PKI may be administered to a subject to treat or prevent a cancer. Such cancers include, but are not limited to, adenocarcinoma, leukemia, lymphoma, melanoma, myeloma, sarcoma, and teratocarcinoma; and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds PKI may be used directly as an antagonist or indirectly as a targeting or delivery mechanism for bringing a pharmaceutical agent to cells or tissues which express PKI.

In another embodiment, an antagonist of PKI may be administered to a subject to prevent or treat an immune disorder. Immune disorders may include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma.

In another embodiment, an antagonist of PKI may be administered to a subject to prevent or treat a developmental disorder. Developmental disorders include, but are not limited to, renal tubular acidosis, Cushing's syndrome, achondroplastic dwarfism, Duchenne and Becker muscular dystrophy, gonadal dysgenesis, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spinal bifida, and congenital glaucoma, cataract, or sensorineural hearing loss.

In another embodiment, a vector expressing the complement of the polynucleotide encoding PKI may be administered to a subject to treat or prevent a cancer including, but not limited to, those described above.

In another embodiment, a vector expressing the complement of the polynucleotide encoding PKI may be administered to a subject to treat or prevent an immune disorder including, but not limited to, those described above.

In another embodiment, a vector expressing the complement of the polynucleotide encoding PKI may be administered to a subject to treat or prevent developmental disorder including, but not limited to, the those described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of PKI may be produced using methods which are generally known in the art. In particular, purified PKI may be used to produce antibodies or to screen libraries of pharmaceutical agents to identify those which specifically bind PKI.

Antibodies to PKI may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with PKI or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to PK and PKI have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of PK and PKI amino acids may be fused with those of another protein such as keyhole limpet hemocyanin and antibody produced against the chimeric molecule.

Monoclonal antibodies to PK and PKI may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256: 495–497; Kozbor, D. et al. (1985) J. Immunol. Methods 81: 31–42; Cote, R. J. et al. (1983) Proc. Natl. Acad. Sci. 80: 2026–2030; Cole, S. P. et al. (1984) Mol. Cell Biol. 62: 109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81: 6851–6855; Neuberger, M. S. et al. (1984) Nature 312: 604–608; Takeda, S. et al. (1985) Nature 314: 452–454). Alternatively, techniques described for the production of single chain antibodies may be adapted, using methods known in the art, to produce PKI-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88: 11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349: 293–299).

Antibody fragments which contain specific binding sites for PK and PKI may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254: 1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between PK and PKI and its specific antibody. A two-site, monoclonal-based immunoassay utilizing monoclonal antibodies reactive to two non-interfering PK and PKI epitopes is preferred, but a competitive binding assay may also be employed (Maddox, supra).

In another embodiment of the invention, the polynucleotides encoding PK and PKI, or any fragment or complement thereof, may be used for therapeutic purposes. In one aspect, the complement of the polynucleotide encoding PK and PKI may be used in situations in which it would be desirable to block the transcription of the mRNA. In particular, cells may be transformed with sequences complementary to polynucleotides encoding PK and PKI. Thus, complementary molecules or fragments may be used to modulate PK and PKI activity, or to achieve regulation of gene function. Such technology is now well known in the art, and sense or antisense oligonucleotides or larger fragments, can be designed from various locations along the coding or control regions of sequences encoding PK and PKI.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding PK and PKI. These techniques are described both in Sambrook et al. (supra) and in Ausubel et al. (supra).

Genes encoding PK and PKI can be turned off by transforming a cell or tissue with expression vectors which express high levels of a polynucleotide or fragment thereof which encodes PK and PKI. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding PK and PKI (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding PK and PKI.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding PK and PKI. Such DNA sequences may be incorporated into a wide variety of vectors with suitable RNA polymerase promoters such as T7 or SP. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15: 462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of PK and PKI, antibodies to PK and PKI, mimetics, agonists, antagonists, or inhibitors of PK and PKI. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinc, acids, etc. Salts tend to be more soluble in aqueous or other protonic solvents than are the corresponding free base forms. In other cases, the preferred preparation may be a lyophilized powder which may contain any or all of the following: 1–50 mM histidine, 0. 1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of PK and PKI, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example PK and PKI or fragments thereof, antibodies of PK and PKI, agonists, antagonists or inhibitors of PK and PKI, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therpeutic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind PK and PKI may be used for the diagnosis of conditions or diseases characterized by expression of PK and PKI, or in assays to monitor patients being treated with PK and PKI, agonists, antagonists or inhibitors. The antibodies useful for diagnostic purposes may be prepared in the same manner as those described above for therapeutics. Diagnostic assays for PK and PKI include methods which utilize the antibody and a label to detect PK and PKI in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring PK and PKI are known in the art and provide a basis for diagnosing altered or abnormal levels of PK and PKI expression. Normal or standard values for PK and PKI expression are established by combining body fluids or cell extracts taken from normal mammalian subjects, preferably human, with antibody to PK and PKI under conditions suitable for binding. The amount of binding may be quantified by various methods, Preferably by Photometric means. Quantities of PK and PKI expressed in subject samples from biopsied tissues are compared with the standard values. Deviation between standard and subject values establishes the parameters for diagnosing disease.

In another embodiment of the invention, the polynucleotides encoding PK and PKI may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of PK and PKI may be correlated with disease. The diagnostic assay may be used to distinguish between absence, presence, and excess expression of PK and PKI, and to monitor regulation of PK and PKI levels during therapeutic intervention.

In one aspect, hybridization with PCR probes which are capable of detecting polynucleotide sequences, including genomic sequences, encoding PK and PKI or closely related molecules, may be used to identify nucleic acid sequences which encode PK and PKI. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding PK and PKI, alleles, or related sequences.

Probes may also be used for the detection of related sequences, and should preferably contain at least 50% of the nucleotides encoding PK and PKI. The hybridization probes of the subject invention may be DNA or RNA and derived from the nucleotide sequences of SEQ ID NOs:2 and 4 or from genomic sequences which include promoter, enhancer elements, and introns of the naturally occurring PK and PKI.

Means for producing specific hybridization probes for DNAs encoding PK and PKI include the cloning of nucleic acid sequences encoding PK and PKI or PK and PKI derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding PK and PKI may be used for the diagnosis of conditions or disorders which are associated with expression of PK and PKI. Examples of such conditions or disorders include cancers such as adenocarcinoma, leukemia, lymphoma, melanoma, myeloma, sarcoma, teratocarcinoma and cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; neuronal disorders such as akathesia, Alzheimer's disease, amnesia, amyotrophic lateral sclerosis, bipolar disorder, catatonia, cerebral neoplasms, dementia, depression, Down's syndrome, tardive dyskinesia, dystonias, epilepsy, Huntington's disease, multiple sclerosis, Parkinson's disease, paranoid psychoses, schizophrenia, and Tourette's disorder; immune disorders such as AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma; and developmental disorders such as renal tubular acidosis, Cushing's syndrome, achondroplastic dwarfism, Duchenne and Becker muscular dystrophy, gonadal dysgenesis, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spinal bifida, and congenital glaucoma, cataract, or sensorineural hearing loss. The polynucleotide sequences encoding PK and PKI may be used in Southern or northern analysis, dot blot, or other membrane-based technologies; in PCR technologies; or in dipstick, pin, ELISA assays or microarrays utilizing fluids or tissues from patient biopsies to detect altered PK and PKI expression. Such qualitative or quantitative methods are well known in the art.

In a particular aspect, the nucleotide sequences encoding PK and PKI may be useful in assays that detect activation or induction of various cancers, particularly those mentioned above. The nucleotide sequences encoding PK and PKI may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding PK and PKI in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of PK and PKI, a normal or standard profile for expression is established. This may be accomplished by combining body fluids or cell extracts taken from normal subjects, either animal or human, with a sequence, or a fragment thereof, which encodes PK and PKI, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding PK and PKI may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of PK and PKI include radiolabeling or biotinylating nucleotides, coamplification of a control nucleic acid, and standard curves onto which the experimental results are interpolated (Melby, P. C. et al. (1993) J. Immunol. Methods, 159: 235–244; Duplaa, C. et al. (1993) Anal. Biochem. 212: 229–236). The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously (to produce a transcript image), and to identify genetic variants, mutations and polymorphisms. This information may be used to determine gene function, understanding the genetic basis of disease, diagnosing disease, and in developing and in monitoring the activities of therapeutic agents.

In further embodiments, oligonucleotides or longer fragments derived from any of the polynucleotide sequences described herein may be used as targets in a microarray. The microarray can be used to monitor the expression level of large numbers of genes simultaneously (to produce a transcript image), and to identify genetic variants, mutations and polymorphisms. This information may be used to determine gene function, understanding the genetic basis of disease, diagnosing disease, and in developing and in monitoring the activities of therapeutic agents.

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover tholigown 5', or 3', sequence, or contain sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell or tissue type or to a normal, developmental, or disease state. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from 2 to one million.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In one aspect, the oligomers are synthesized at designated areas on a substrate using a light-directed chemical process. The substrate may be paper, nylon or other type of membrane, filter, chip, glass slide, or any other suitable solid support.

In another aspect, the oligonucleotides may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot or slot blot (HYBRIDOT apparatus, GIBCO/BRL) may be used to arrange and link cDNA fragments or oligonucleotides to the surface of a substrate using a vacuum system, thermal, UV, mechanical or chemical bonding procedures. In yet another aspect, an array may be produced by hand or using available devices, materials, and machines (including BRINKMANN multichannel pipettors or robotic instruments) and may contain 8, 24, 96, 384, 1536 or 6144 oligonucleotides, or any other multiple from 2 to one million which lends itself to the efficient use of commercially available instrumentation.

In order to conduct sample analysis using the microarrays, polynucleotides are extracted from a biological sample. The biological samples may be obtained from any bodily fluid (blood, urine, saliva, phlegm, gastric juices, etc.), cultured cells, biopsies, or other tissue preparations. To produce probes, the polynucleotides extracted from the sample are used to produce nucleic acid sequences which are complementary to the nucleic acids on the microarray. If the microarray consists of cDNAs, antisense RNAs (aRNA) are appropriate probes. Therefore, in one aspect, mRNA is used to produce cDNA which, in turn and in the presence of fluorescent nucleotides, is used to produce fragment or oligonucleotide aRNA probes. These fluorescently labeled probes are incubated with the microarray so that the probe sequences hybridize to the cDNA oligonucleotides of the microarray. In another aspect, complementary nucleic acid sequences are used as probes and can also include polynucleotides, fragments, complementary, or antisense sequences produced using restriction enzymes, PCR technologies, and Oligolabeling or TransProbe kits (Pharmacia) well known in the area of hybridization technology.

Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. A detection system may be used to measure the absence, presence, and amount of hybridization for all of the distinct sequences simultaneously. This data may be used for large scale correlation studies or functional analysis of the sequences, mutations, variants, or polymorphisms among samples (Heller, R. A. et al., (1997) Proc. Natl. Acad. Sci. 94: 2150–55).

In another embodiment of the invention, the nucleic acid sequences which encode PK and PKI may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7: 127–134, and Trask, B. J. (1991) Trends Genet. 7: 149–154.

Fluorescent in situ hybridization (FISH as described in Verma et al. (1988) *Human Chromosomes: A Manual of Basic Techniques,* Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding PK and PKI on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336: 577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, PK and PKI, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between PK and PKI and the agent being tested, may be measured.

Another technique for drug screening which may be used provides for high throughput screening of compounds having suitable binding affinity to the protein of interest as described in published PCT application WO84/03564. In this method, as applied to PK and PKI large numbers of different small test compounds are synthesized on a solid substrate, such as plastic pins or some other surface. The test compounds are reacted with PK and PKI, or fragments thereof, and washed. Bound PK and PKI is then detected by methods well known in the art. Purified PK and PKI can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding PK and PKI specifically compete with a test compound for binding PK and PKI. In this manner, the antibodies can be used to detect the presence of any peptide which shares one or more antigenic determinants with PK and PKI.

In additional embodiments, the nucleotide sequences which encode PK and PKI may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

Synorat03

For the CDNA library SYNORAT03, the rheumatoid wrist synovium from a 56 year-old female was used for CDNA library construction and was obtained T. Kenny, U C Davis. The frozen tissue was homogenized using a Polytron PT-3000 homogenizer (Brinkmann Instruments, Westbury N.J.) and lysed in a buffer containing guanidinium isothiocyanate. The lysate was centrifuged over a 5.7 M CsCl cushion using an Beckman SW28 rotor in an L8-70M ultracentrifuge (Beckman Instruments) for 18 hours at 25,000 rpm at ambient temperature. The RNA was extracted twice with acid phenol pH 4.0 using the reagents and extraction procedures as supplied in the Stratagene RNA Isolation Kit (Catalog #200345; Stratagene). RNA was precipitated using 0.3 M sodium acetate and 2.5 volumes of ethanol, resuspended in water and DNase treated for 15 min at 37° C. The RNA was isolated using the OLIGOTEX kit (QIAGEN Inc, Chatsworth Calif.) and used to construct the cDNA library.

The RNA was used to construct cDNAs according to the recommended protocols in the SUPERSCRIPT plasmid system for cDNA and plasmid cloning (Catalog #18248-013, Gibco BRL, Grand Island N.Y.). cDNAs were fractionated on a Sepharose CL4B column (Catalog #275105, Pharmacia) to obtain sequences exceeding 400 bp and ligated into the plasmid, PSPORT1. The plasmid was subsequently transformed into DH5a competent cells (Catalog #18258-012, Gibco BRL) for amplification.

Colnnot11

The COLNNOT11 cDNA library was constructed from microscopically normal colon tissue obtained from a 60-year old Caucasian male who had undergone a left hemicolectomy to remove a tumor in a different part of his bowel. Pathology indicated a grade 2 adenocarcinoma which extended through the submucosa and superficially into the muscularis propria. The margins of the resection were free of involvement, however one (of 9) regional lymph nodes contained metastatic adenocarcinoma. The patient presented with blood in his stool and changing bowel habits. Patient history included previous diagnoses of depressive disorder and thrombophlebitis, accompanied by inflammatory polyarthropathies and inflammatory disease of the prostate. Previous surgeries included a vasectomy and resection of the rectum. Family history included malignant colon neoplasm in a sibling. Patient medications included SELDANE (terfenadin; Marion Merrell Dow, Inc., Kansas City, Mo.). The frozen tissue was homogenized and lysed using a Polytron PT-3000 homogenizer (Brinkmann Instruments, Westbury, N.Y.) in guanidinium isothiocyanate solution. The lysate was centrifuged over a 5.7 M CsCl cushion using an SW28 rotor in an L8-70M ultracentrifuge (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and DNase treated at 37° C. The RNA extraction was repeated with acid phenol pH 4.7 and precipitated with sodium acetate and ethanol as before. The mRNA was then isolated using the OLIGOTEX kit (QIAGEN, Inc., Chatsworth, Calif.) and used to construct the cDNA library.

The RNA was handled according to the recommended protocols in the SUPERSCRIPT plasmid system for cDNA synthesis and plasmid cloning (Catalog #18248-013; Gibco/BRL). The cDNAs were fractionated on a Sepharose CLAB column (Catalog #275105-01, Pharmacia), and those cDNAs exceeding 400 bp were ligated into PSPORT1. The plasmid PSPORT1 was subsequently transformed into DH5a competent cells (Catalog #18258-012, Gibco/BRL).

Kidnnot25

The KIDNNOT25 CDNA library was constructed using 2 micrograms of poly RNA isolated from kidney tissue removed from the left lower kidney pole of a 42-year-old Caucasian female during nephrouretherectomy. Pathology indicated the sample to be benign. Pathology for the associated diseased tissue indicated benign simple cysts, slight hydronephrosis, and nephrolithiasis with stones ranging in size. The patient presented with calculus of the kidney, abnormal kidney function study, and an unspecified congenital kidney abnormality. Patient history includes benign hypertension and calculus of the kidney. Previous surgeries included an electroshock wave lithotripsy of an unspecified site. Patient medications included BICITA, HCTZ, ALLOPURINOR, CEPHALEXIN, and DARVOCET 100. Family history included benign hypertension in the father and alcohol abuse in the sibling(s). cDNA synthesis was initiated using a NotI-oligo(dT) primer.

The mRNA was handled according to the recommended protocols in the SUPERSCRIPT plasmid system for cDNA synthesis and plasmid cloning (Cat. #18248-013, Gibco/BRL). The cDNAs were fractionated on a SEPHAROSE CL4B column (Cat. #275105-01; Pharmacia), and those cDNAs exceeding 400 bp were ligated into pINCY 1. The plasmid pINCY 1 was subsequently transformed into DH5a competent cells (Cat. #18258-012; Gibco/BRL).

II Isolation and Sequencing of cDNA Clones

Synorat03

Plasmid DNA was released from the cells and purified using the Miniprep kit (Catalog #77468; Advanced Genetic Technologies Corporation, Gaithersburg Md.). This kit consists of a 96-well block with reagents for 960 purifications. The recommended protocol was employed except for the following changes: 1) the 96 wells were each filled with only 1 ml of sterile Terrific Broth (Catalog #22711, GIBCO/BRL™) with carbenicillin at 25 mg/L and glycerol at 0.4%; 2) the bacteria were cultured for 24 hours after the wells were inoculated and then lysed with 60 µl of lysis buffer; 3) a centrifugation step employing the Beckman GS-6R rotor at 2900 rpm for 5 minutes was performed before the contents of the block were added to the primary filter plate; and 4) the optional step of adding isopropanol to TRIS buffer was not routinely performed. After the last step in the protocol, samples were transferred to a Beckman 96-well block for storage.

The cDNAs were sequenced by the method of Sanger F and AR Coulson (1975; J Mol Biol 94: 441f), using a MICROLAB 2200 (Hamilton, Reno, Nev.) in combination with four Peltier thermal cyclers (PTC200 from MJ Research, Watertown, Mass.) and Applied Biosystems 377 or 373 DNA sequencing systems, and the reading frame was determined.

Colnnot11 and Kidnnot25

Plasmid DNA was released from the cells and purified using the R.E.A.L. PREP 96 plasmid kit for rapid extraction alkaline lysis plasmid minipreps (Catalog #26173, QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, GIBCO/BRL™) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, *J. Mol. Biol.* 94: 441f), using a MICROLAB 2200 (Hamilton, Reno, Nev.) in combination with Peltier thermal cyclers (PTC200 from MJ Research, Watertown, Mass.) and Applied Biosystems 377 DNA sequencing systems, and the reading frame was determined.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul SF (1993) J Mol Evol 36: 290–300; Altschul, SF et al (1990) J Mol Biol 215: 403–10).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith, R. F. and T. F. Smith (1992; Protein Engineering 5: 35–51), incorporated herein by reference, can be used when dealing with primary sequence patterns and secondary structure gap penalties. As disclosed in this application, sequences have lengths of at least 49 nucleotides and no more than 12% uncalled bases (where N is recorded rather than A, C, G, or T).

The BLAST approach, as detailed in Karlin and Altschul (1993; Proc Nat Acad Sci 90: 5873–7) and incorporated herein by reference, searches matches between a query sequence and a database sequence, to evaluate the statistical significance of any matches found, and to report only those matches which satisfy the user-selected threshold of significance. In this application, threshold is set at 10–25 for nucleotides and 10–14 for peptides.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) Supra; Altschul, S. F. et al. (1990) Supra) are used to search for identical or related molecules in nucleotide databases such as GenBank or the LIFESEQ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding PK and PKI occurs. Abundance and percent abundance are also reported. Abundance directly reflects the number of times a particular transcript is represented in a cDNA library, and percent abundance is abundance divided by the total number of sequences examined in the cDNA library.

V Extension of PK and PKI Encoding Polynucleotides

The nucleic acid sequences of the Incyte Clone 1762 and 2456290 were used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 software (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (GIBCO/BRL) were used to extend the sequence If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier thermal cycler (PTC200; M.J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK (QIAGEN Inc., Chatsworth, Calif.), and trimmed of overhangs using Klenow enzyme to facilitate religation and cloning.

After ethanol precipitation, the products were redissolved in 13 μl of ligation buffer 1 μl T4-DNA ligase (15 units) and 1 μl T4 polynucleotide kinase were added, and the mixture was incubated at room temperature for 2–3 hours or overnight at 16° C. Competent E. coli cells (in 40 μl of appropriate media) were transformed with 3 μl of ligation mixture and cultured in 80 μl of SOC medium (Sambrook et al., supra). After incubation for one hour at 37° C., the E. coli mixture was plated on Luria Bertani (LB)-agar (Sambrook et al., supra) containing 2× Carb. The following day, several colonies were randomly picked from each plate and cultured in 150 μl of liquid LB/2× Carb medium placed in an individual well of an appropriate, commercially-available, sterile 96-well microtiter plate. The following day, 5 μl of each overnight culture was transferred into a non-sterile 96-well plate and after dilution 1:10 with water, 5 μl of each sample was transferred into a PCR array.

For PCR amplification, 18 μl of concentrated PCR reaction mix (3.3x) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequences of SEQ ID NO:2, 5 and 8 are used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2, 5, and 8 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 Software (National Biosciences), labeled by combining 50 pmol of each oligomer and 250 μCi of [γ-$^{32}$P] adenosine triphosphate (Amersham) and T4 polynucleotide kinase (DuPont NEN, Boston, Mass.). The labeled oligonucleotides are substantially purified with SEPHADEX G-25 superfine resin column (Pharmacia & Upjohn). A aliquot containing 10$^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1x saline sodium citrate and 0.5% sodium dodecyl sulfate. After XOMAT AR film (Kodak, Rochester, N.Y.) is exposed to the blots, or the blots are exposed to a Phosphoimager cassette (Molecular Dynamics, Sunnyvale, Calif.) for several hours, hybridization patterns are compared visually.

VII Microarrays

To produce oligonucleotides for a microarray, SEQ ID NO:2 and SEQ ID NO:4 are examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized in the presence of fluorescent or radioactive nucleotides and arranged on the surface of the substrate. When the substrate is a silicon chip, a light-directed chemical process is used for deposition (Chee, M. et al., PCT/WO95/11995, incorporated herein by reference).

In the alternative, a chemical coupling procedure and an ink jet device is used to synthesize oligomers on the surface of a substrate (Baldeschweiler, J. D. et al., PCT/WO95/25 116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. A typical array may be produced by hand or using available materials and machines and contain grids of 8 dots, 24 dots, 96 dots, 384 dots, 1536 dots or 6144 dots. After hybridization, the microarray is washed to remove nonhybridized probes, and a detection device as simple as X-ray film or complicated as a light scanner is used to determine the levels and patterns of radioactivity or fluorescence. Scanned fluorescent images are examined to determine degree of complementarity and the relative abundance/expression level of each oligonucleotide sequence in the microarray.

VIII Complementary Polynucleotides

Sequence complementary to the HUBI-encoding sequence, or any part thereof, is used to decrease or inhibit expression of naturally occurring PK and PKI. Although use of oligonucleotides comprising from about 15 to about 30 base-pairs is described, essentially the same procedure is used with smaller or larger sequence fragments. Appropriate oligonucleotides are designed using OLIGO 4.06 software and the coding sequence of PK and PKI. To inhibit transcription, a complementary oligonucleotide is designed from the most unique 5' sequence and used to prevent promoter binding to the coding sequence. To inhibit translation, a complementary oligonucleotide is designed to prevent ribosomal binding to the transcript encoding PK and PKI.

IX Expression of PK and PKI

Expression of PK and PKI is accomplished by subcloning the cDNAs into appropriate vectors and transforming the vectors into host cells. In this case, the cloning vector is also used to express PK and PKI in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of PK and PKI into the bacterial growth media which can be used directly in the following assay for activity.

X Demonstration of PK and PKI Activity

PK

PK activity was assayed by taking samples were fractionated on SDS-polyacrylamide gel then washed with 20% (v/v) propan-2-ol to remove SDS. The gel was denatured with 6 M guanidine HCl, then renatured in 5 mM 2-mercaptoethanol, 50 mM Tris-HCl, p (10% (w/v) acrylamide) containing GST-LT-R(CD) fusion protein. The gel was pH 8.0, and 0.04% (v/v) Tween 40. Renaturation was followed by washing at 4° C. for 30 min with two changes of buffer (20 mM HEPES, pH 7.4, 0.2 mM NaF, 0.1 mM sodium orthovanadate), and incubated at 22° C. for 3 h in the kinase reaction buffer containing 50 μCi of [γ-$^{32}$P] ATP. After removal of unreacted [γ-$^{32}$P]ATP, protein kinases were visualized by autoradiography of the dried gel. Signals due to protein kinases were also detected and quantified using a PHOSPHORIMAGER (Molecular Dynamics) to allow comparison of signal strengths (Mei-Yi et al. (1997) J. Biol. Chem. 272 (27): 17154–17159).

PKI-1 and PKI-2

Assays for PKI-1 and PKI-2 were conducted for 2 minutes at 30° C. in a reaction mixture of final volume 0.08 ml containing 30 mM Tris-HCL (pH 7.4), 2 mM magnesium acetate, 1uM cGMP, 0.2 mM [γ-$^{32}$P]ATP (215–300 cpm/pmol), substrate protein or peptide as indicated below, the indicated concentrations of the various inhibitor peptides, 3 mM 2-mercaptoethanol, 0.3 mg/ml bovine serum albumin, and 0.2–0.4 μg/ml (1.3–2.6 nM) cGMP-dependent protein kinase. Either 1.5 μM histone H2B, 20 μM (ALA$^{34}$)H2B, or 150 μM Kemptide was used as substrate. These concentrations are slightly below the $K_m$ values of cGMP-dependent protein kinase for the respective substrates. Under these assay conditions, the conversion of histone H2B, (ALA$^{34}$) H2B, and Kemptide to product were approximately 55%, 18%, and 3%, respectively. Utilization of [γ-$^{32}$P]ATP was approximately 2% or less in each case. When analogs of PKI amide were tested as possible substrates of cGMP-dependent protein kinases, they were used at a final concentration of 50 μM, and the cGMP-dependent kinase was used at a concentration of 20 μg/ml. cGMP-dependent protein kinase was preincubated with buffer, cGMP, Mg$^{2+}$, [γ-$^{32}$P]ATP, and inhibitor peptide for 2 min at 30° C., after which the reaction was initiated by the addition of protein or peptide substrate. Reactions were terminated and $^{32}$P-phosphopeptide or -histone was quantitated in 50 μL aliquots of reaction mixture by the phosphocellulose paper method using a phosphoric acid washing procedure. The highest amount of peptide substrates and inhibitors used were well over an order of magnitude lower than the capacity of phosphocellulose paper squares for binding peptides (Glass, D. B. et al. J Biol. Chem. 261: 12166–12171).

XI Production of PK and PKI Specific Antibodies

PK and PKI that is substantially purified using PAGE electrophoresis (Sambrook, supra), or other purification techniques, is used to immunize rabbits and to produce antibodies using standard protocols. The amino acid sequences deduced from SEQ ID NO:1, SEQ ID NO:4, and SEQ ID NO:7 are analyzed using DNASTAR software (DNASTAR Inc.) to determine regions of high immunogenicity and corresponding oligopeptides are synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems 431A peptide synthesizer using fmoc-chemistry, and coupled to keyhole limpet hemocyanin (KLH, Sigma, St. Louis, MO) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring PK and PKI Using Specific Antibodies

Naturally occurring or recombinant PK and PKI is substantially purified by immunoaffinity chromatography using antibodies specific for PK and PKI. An immunoaffinity column is constructed by covalently coupling PK and PKI antibody to an activated chromatographic resin, such as CNBr-activated SEPHAROSE (Pharmacia & Upjohn). After the coupling, the resin is blocked and washed according to the manufacturer's instructions.

Media containing PK and PKI is passed over the immunoaffinity column, and the column is washed under conditions that allow the preferential absorbance of PK and PKI (e.g., high ionic strength buffers in the presence of detergent). The column is eluted under conditions that disrupt antibody/HUBI binding (eg, a buffer of pH 2–3 or a high concentration of a chaotrope, such as urea or thiocyanate ion), and PK and PKI is collected.

XIII Identification of Molecules Which Interact with PK and PKI

PK and PKI or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled PK and PKI, washed and any wells with labeled PK and PKI complex are assayed. Data obtained using different concentrations of PK and PKI are used to calculate values for the number, affinity, and association of PK and PKI with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence encoding a human protein kinase (PK) comprising the amino acid sequence of SEQ ID NO:1 or an enzymatically active fragment thereof.

2. An isolated and purified composition comprising the polynucleotide sequence of claim 1.

3. An isolated and purified polynucleotide sequence which hybridizes under high stringent conditions and encodes the PK of SEQ ID NO:1 to the polynuclcotide sequence of claim 1.

4. A polynucleotide sequence which is complementary to the polynucleotide sequence of claim 1.

5. An isolated and purified polynucleotide sequence comprising SEQ ID NO:2, encoding an enzymatically active fragment of SEQ ID NO:1.

6. A composition comprising the polynucleotide sequence of claim 5.

7. An isolated and purified polynucleotide sequence which is complementr to the polynucleotide sequence of claim 5.

8. An expression vector the comprising polynucleotide sequence of claim 1.

9. A host cell comprising the expression vector of claim 8.

10. A method for producing protein kinase having the amino acid sequence of SEQ ID NO:1 or enzymatically active fragment thereof, the method comprising the steps of:

a) culturing the host cell of claim 9 under conditions suitable for the expression of the polypeptide; and b) recovering the polypeptide from the host cell culture.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 345 amino acids (B) TYPE: amino acid
(C) STRANDEDNESS: single
(D) TOPOLOGY: linear (vii) IMMEDIATE SOURCE:
(A) LIBRARY: KIDNNOT25
(B) CLONE: 353694

(xi) SEQUENCE DESCRIPTION: SEQ ID NO:1:

```
Met Asn Leu Ala Leu Ala Gly Asp Ile Leu Ala Ala Gly Gln Asp Ala
 1               5                  10                  15
His Cys Gln Leu Leu Arg Phe Gln Ala His Gln Gln Gly Asn Lys
            20                  25                  30
Ala Glu Lys Ala Gly Ser Lys Glu Gln Gly Pro Arg Gln Arg Lys Gly
            35                  40                  45
Ala Ala Pro Ala Glu Lys Lys Cys Gly Ala Glu Thr Gln His Glu Gly
50                  55                  60
Leu Glu Leu Arg Val Glu Asn Leu Gln Ala Val Gln Thr Asp Phe Ser
65                  70                  75                  80
Ser Asp Pro Leu Gln Lys Val Val Cys Phe Asn His Asp Asn Thr Leu
                85                  90                  95
Leu Ala Thr Gly Gly Thr Asp Gly Tyr Val Arg Val Trp Lys Val Pro
                100                 105                 110
Ser Leu Glu Lys Val Leu Glu Phe Lys Ala His Glu Gly Glu Ile Glu
            115                 120                 125
Asp Leu Ala Leu Gly Pro Asp Gly Lys Leu Val Thr Val Gly Arg Asp
130                 135                 140
Leu Lys Ala Ser Val Trp Gln Lys Asp Gln Leu Val Thr Gln Leu His
145                 150                 155                 160
Trp Gln Glu Asn Gly Pro Thr Phe Ser Thr Pro Tyr Arg Tyr Gln
                165                 170                 175
Ala Cys Arg Phe Gly Gln Val Pro Asp Gln Pro Ala Gly Leu Arg Leu
            180                 185                 190
Phe Thr Val Gln Ile Pro His Lys Arg Leu Arg Gln Pro Pro Pro Cys
            195                 200                 205
Tyr Leu Thr Ala Trp Asp Gly Ser Asn Phe Leu Pro Leu Arg Thr Lys
    210                 215                 220
Ser Cys Gly His Glu Val Val Ser Cys Leu Asp Val Ser Glu Ser Gly
225                 230                 235                 240
Thr Phe Leu Gly Leu Gly Thr Val Thr Gly Ser Val Ala Ile Tyr Ile
                245                 250                 255
Ala Phe Ser Leu Gln Cys Leu Tyr Tyr Val Arg Glu Ala His Gly Ile
            260                 265                 270
Val Val Thr Asp Val Ala Phe Leu Pro Glu Lys Gly Arg Gly Pro Glu
    275                 280                 285
Leu Leu Gly Ser His Glu Thr Ala Leu Phe Ser Val Ala Val Asp Ser
        290                 295                 300
Arg Cys Gln Leu His Leu Leu Pro Ser Arg Arg Ser Val Pro Val Trp
305                 310                 315                 320
Leu Leu Leu Leu Leu Cys Val Gly Leu Ile Ile Val Thr Ile Leu Leu
                325                 330                 335
Leu Gln Ser Ala Phe Pro Gly Phe Leu
            340                 345
```

(2) INFORMATION FOR SEQ ID NO:2:

(i) SEQUENCE CHARACTERISTICS:
    (A) LENGTH: 1977 base pairs
    (B) TYPE: nucleic acid
    (C) STRANDEDNESS: single
    (D) TOPOLOGY: linear (vii) IMMEDIATE SOURCE:
    (A) LIBRARY: KIDNNOT25
    (B) CLONE: 3453694

(xi) SEQUENCE DESCRIPTION: SEQ ID NO:2:

```
TGTAAAATAG AGGTAATAAT CCCAGTCCTG CTCACTGTGT AGATTTGTGA GGCCCAAATG      60
AGAGAAAAAA GACTCGAGAA ACCCTTGTGA ACTAGAACGT GCAGAAAGCA AAGGGGTAAG     120
ACATCAGACT CTTCCCTAAA CGTGCTCTCT GGGCACCCCT GAACTTGCTC ATCCGGGTTC     180
CCCCTCCCAC AGCACTTTCT GCAGCTAGAG CTGATTAATG GGCGCTTGAG TGCCTCCTTG     240
CTGCACTCCC ATGACACAGA GACACGGGCC ACCATGAACT TGGCACTGGC TGGTGACATC     300
CTTGCTGCAG GGCAGGATGC CCACTGTCAG CTCCTGCGCT TCCAGGCACA TCAACAGCAG     360
GGCAACAAGG CAGAGAAGGC CGGTTCCAAG GAGCAGGGGC CTCGACAAAG GAAGGGAGCA     420
GCCCCAGCAG AGAAGAAATG TGGAGCGGAA ACCCAGCACG AGGGGCTAGA ACTCAGGGTA     480
GAGAATTTGC AGGCGGTGCA GACAGACTTT AGCTCCGATC CACTGCAGAA AGTTGTGTGC     540
TTCAACCACG ATAATACCCT GCTTGCCACT GGAGGAACAG ATGGCTACGT CCGTGTCTGG     600
AAGGTGCCCA GCCTGGAGAA GGTTCTGGAG TTCAAAGCCC ACGAAGGGGA GATTGAAGAC     660
CTGGCTTTAG GGCCTGATGG CAAGTTGGTA ACCGTGGGCC GGGACCTTAA GGCCTCTGTG     720
TGGCAGAAGG ATCAGCTGGT GACACAGCTG CACTGGCAAG AAAATGGACC CACCTTTTCC     780
AGCACACCTT ACCGCTACCA GGCCTGCAGG TTTGGGCAGG TTCCAGACCA GCTGCTGGC     840
CTGCGACTCT TCACAGTGCA AATTCCCCAC AAGCGCCTGC GCCAGCCCCC TCCCTGCTAC     900
CTCACAGCCT GGGATGGCTC CAACTTCTTG CCCCTTCGGA CCAAGTCCTG TGGCCATGAA     960
GTCGTCTCCT GCCTCGATGT CAGTGAATCC GGCACCTTCC TAGGCCTGGG CACAGTCACT    1020
GGCTCTGTTG CCATCTACAT AGCTTTCTCT CTCCAGTGCC TCTACTACGT GAGGGAGGCC    1080
CATGGCATTG TGGTGACGGA TGTGGCCTTT CTACCTGAGA AGGGTCGTGG TCCAGAGCTC    1140
CTTGGGTCCC ATGAAACTGC CCTGTTCTCT GTGGCTGTGG ACAGTCGTTG CCAGCTGCAT    1200
CTGTTGCCCT CACGGCGGAG TGTTCCTGTG TGGCTCCTGC TCCTGCTGTG TGTCGGGCTT    1260
ATTATTGTGA CCATCCTGCT GCTCCAGAGT GCCTTTCCAG GTTTCCTTTA GCTTCCCTGC    1320
TTCCTGGGAA TCAGGAGCCT GGACACTGCC ATCTCTAGAG CAGAGTGGAG GCCTGGACTC    1380
CCTTTGCTCA CTCCATTCGG GTCCACAGCT GAGGTTGCCT CTGACAAGAT GAATGGGCAC    1440
TGCCTGCCCT TCTAGTGAAA AGGCTTGGCT ATGGCCCTGT GTGACTCCAG GTCCCAGGAA    1500
CCTTGCCTTC GTCATCTGTG GATCCATCCA GAACAGCGGT ATCTGAAGCC CAGGCCATAC    1560
TCCCTGCCTC CTTTCTTCTG CCTACCAGAG GCTCCAGAGT TGAGCTTGTC CTTATCTAGA    1620
AACATGTGAA GATGCCCAAG AGCCTGGAGG CACTGCTGTC CTTCCTGCAG AAACAGTTTC    1680
TCCTCCTCCC CTCAGCCTTG TGGCCAGTTC CTCTTCACAT GAAGCCCCTG GCATTTGCTG    1740
GGGAAGGGAC TGGCCTGGTA CTTGCTGTTA GGGCAGGAAG GGCAAAAGG AAGACTTGGG    1800
TAGTAATCTG GGGGTTCAGA TGGGTAGCAC TAAGCCAGCT GGCCTAAAGA TGCAATAAGT    1860
TCCTAGGTAG TCTACCCTTA CCTTGAGGAA TGGGAAAATG AACCTCAGCC CATTAGGCAG    1920
GAAAAGTTGA TATTTAATAA ACAAGGAAAG AGTGAACTGA GACCCCAAAA AAAAAAA       1977
```

(2) INFORMATION FOR SEQ ID NO:3:

(i) SEQUENCE CHARACTERISTICS:
        (A) LENGTH: 365 amino acids
        (B) TYPE: amino acid
        (C) STRANDEDNESS: single
        (D) TOPOLOGY: linear (vii) IMMEDIATE SOURCE:
        (A) LIBRARY: KIDNNOT25
        (B) CLONE: 353694

(xi) SEQUENCE DESCRIPTION: SEQ ID NO:3:

```
Met Thr Ile Phe Gly Gly Gly Gln Ser Lys Lys Ala Pro Leu Ile Gly
 1               5                  10                  15

Glu Ser Gly Ile Pro Ala Tyr Cys Leu Lys Thr Ile Gly Ser Arg His
            20                  25                  30

Ile Leu Val Ala Gly Gly Gly Ala Ser Lys Thr Gly Val Leu Asn
            35                  40                  45

Glu Ile Gln Thr His Leu Phe Thr Thr Gly Ser Ala Asn Gln Asp Val
50                  55                  60

Gly Phe Gln Ser Lys Cys Val Gly Lys Phe Asp Thr Gly Ser Met Ala
65                  70                  75                  80

Thr Met Asn Met Asp Val Ala Cys Ala Phe Asp Glu Ile Ser Ala Lys
                85                  90                  95

Tyr Val Ile Ala Ala Gly Gln Glu Asn Leu Cys Ala Leu Tyr Met Thr
                100                 105                 110

Arg Ala Phe Lys Leu Asn Glu Glu Asn Glu Cys Leu Ser Phe Glu Ile
                115                 120                 125

Gln Lys Val Ser Gln Val Arg Ser Asp Phe His Ala Ser Asn Ser Tyr
130                 135                 140

Gln Lys Cys Val Arg Phe Asp Lys Ser Ser Arg Gly Lys Ile Phe Ala
145                 150                 155                 160

Thr Gly Gly Ala Asp Gly His Ile Arg Ile Trp Asn Ala Gln Ile Val
                165                 170                 175

Phe Arg Ala Glu Asn Glu Asp Ala Gln Pro Ile Leu Thr Ile Gln Ala
                180                 185                 190

His Lys Ala Asp Val Asp Asp Ile Asp Phe Ser Lys Asp Ser Lys Thr
                195                 200                 205

Ile Ile Ser Val Gly Ala Glu Gly Ala Phe Ile Trp Ser Thr Gln Thr
210                 215                 220

Gly Ala Arg Leu Leu Asp Leu Gln Phe Pro Ile Glu Ile Ser Arg Gly
225                 230                 235                 240

Phe Lys Ser Ile Ser Ser Leu Ala Val Ser Asp Cys Gly Asn Phe Thr
                245                 250                 255

Ala Val Gly Thr Met Ser Gly Ser Val Leu Val Phe Asp Thr His Glu
                260                 265                 270

Cys Arg Arg Leu Tyr Phe Ser Pro Glu Ser His Gly Leu Phe Val Thr
                275                 280                 285

Gly Ile Glu Phe Val Ser Arg Thr Ser Pro Ser Ile Cys Glu Asp Ile
                290                 295                 300

Gln Ser Glu Thr Pro Gly Ile Ala Ser Gly Phe Gln Ser Ala Val Val
305                 310                 315                 320

Thr Leu Ala Ala Asp Lys Thr Met Gln Leu His Arg Val Pro Tyr Pro
                325                 330                 335

Gln Pro Gln Pro Phe Ser Glu Tyr Leu Leu Ile Ile Ser Leu Val Cys
                340                 345                 350
```

```
Leu Ile Phe Thr Trp Leu Ser Ser Phe Phe Ile Val Ser
    355                 360                 365

(2) INFORMATION FOR SEQ ID NO:4:

(i) SEQUENCE CHARACTERISTICS:
        (A) LENGTH: 484 amino acids
        (B) TYPE: amino acid
        (C) STRANDEDNESS: single
        (D) TOPOLOGY: linear (vii) IMMEDIATE SOURCE:
        (A) LIBRARY: COLNNOT11
        (B) CLONE: 701698

(xi) SEQUENCE DESCRIPTION: SEQ ID NO:4:

Met Ala Ala Thr Glu Pro Glu Leu Leu Asp Asp Gln Glu Ala Lys Arg
1               5                   10                  15

Glu Ala Glu Thr Phe Lys Glu Gln Gly Asn Ala Tyr Tyr Ala Lys Lys
                20                  25                  30

Asp Tyr Asn Glu Ala Tyr Asn Tyr Tyr Thr Lys Ala Ile Asp Met Cys
            35                  40                  45

Pro Lys Asn Ala Ser Tyr Tyr Gly Asn Arg Ala Ala Thr Leu Met Met
        50                  55                  60

Leu Gly Arg Phe Arg Glu Ala Leu Gly Asp Ala Gln Gln Ser Val Arg
65                  70                  75                  80

Leu Asp Asp Ser Phe Val Arg Gly His Leu Arg Glu Gly Lys Cys His
                85                  90                  95

Leu Ser Leu Gly Asn Ala Met Ala Ala Cys Arg Ser Phe Gln Arg Ala
                100                 105                 110

Leu Glu Leu Asp His Lys Asn Ala Gln Ala Gln Gln Glu Phe Lys Asn
            115                 120                 125

Ala Asn Ala Val Met Glu Tyr Glu Lys Ile Ala Glu Thr Asp Phe Glu
        130                 135                 140

Lys Arg Asp Phe Arg Lys Val Val Phe Cys Met Asp Arg Ala Leu Glu
145                 150                 155                 160

Phe Ala Pro Ala Cys His Arg Phe Lys Ile Leu Lys Ala Glu Cys Leu
                165                 170                 175

Ala Met Leu Gly Arg Tyr Pro Glu Ala Gln Ser Val Ala Ser Asp Ile
                180                 185                 190

Leu Arg Met Asp Ser Thr Asn Ala Asp Ala Leu Tyr Val Arg Gly Leu
            195                 200                 205

Cys Leu Tyr Tyr Glu Asp Cys Ile Glu Lys Ala Val Gln Phe Phe Val
210                 215                 220

Gln Ala Leu Arg Met Ala Pro Asp His Glu Lys Ala Cys Ile Ala Cys
225                 230                 235                 240

Arg Asn Ala Lys Ala Leu Lys Ala Lys Lys Glu Asp Gly Asn Lys Ala
                245                 250                 255

Phe Lys Glu Gly Asn Tyr Lys Leu Ala Tyr Glu Leu Tyr Thr Glu Ala
                260                 265                 270

Leu Gly Ile Asp Pro Asn Asn Ile Lys Thr Asn Ala Lys Leu Tyr Cys
            275                 280                 285

Asn Arg Gly Thr Val Asn Ser Lys Leu Arg Lys Leu Asp Asp Ala Ile
        290                 295                 300

Glu Asp Cys Thr Asn Ala Val Lys Leu Asp Asp Thr Tyr Ile Lys Ala
305                 310                 315                 320
```

```
Tyr Leu Arg Arg Ala Gln Cys Tyr Met Asp Thr Glu Gln Tyr Glu Glu
            325                 330                 335

Ala Val Arg Asp Tyr Glu Lys Val Tyr Gln Thr Glu Lys Thr Lys Glu
            340                 345                 350

His Lys Gln Leu Leu Lys Asn Ala Gln Leu Glu Leu Lys Lys Ser Lys
            355                 360                 365

Arg Lys Asp Tyr Tyr Lys Ile Leu Gly Val Asp Lys Asn Ala Ser Glu
            370                 375                 380

Asp Glu Ile Lys Lys Ala Tyr Arg Lys Ala Leu Met His His Pro
385                 390                 395                 400

Asp Arg His Ser Gly Ala Ser Ala Glu Val Gln Lys Glu Glu Glu Lys
            405                 410                 415

Lys Phe Lys Glu Val Gly Glu Ala Phe Thr Ile Leu Ser Asp Pro Lys
            420                 425                 430

Lys Lys Thr Arg Tyr Asp Ser Gly Gln Asp Leu Asp Glu Glu Gly Met
            435                 440                 445

Asn Met Gly Asp Phe Asp Pro Asn Asn Ile Phe Lys Ala Phe Phe Gly
450                 455                 460

Gly Pro Gly Gly Phe Ser Phe Glu Ala Ser Gly Pro Gly Asn Phe Phe
465                 470                 475                 480

Phe Gln Phe Gly
```

(2) INFORMATION FOR SEQ ID NO:5:

(i) SEQUENCE CHARACTERISTICS:
        (A) LENGTH: 1811 base pairs
        (B) TYPE: nucleic acid
        (C) STRANDEDNESS: single
        (D) TOPOLOGY: linear (vii) IMMEDIATE SOURCE:
        (A) LIBRARY: COLNNOT11
        (B) CLONE: 701698

(xi) SEQUENCE DESCRIPTION: SEQ ID NO:5:

```
GCTCTTCACC GCCGGCCTCC CACCCAGCTC TCTGGTCCCG GCGGTAAGAT GGCGGCTGCC     60

GCGGAGTGCG ATGTGGTAAT GGCGGCGACC GAGCCGGAGC TGCTCGACGA CCAAGAGGCG    120

AAGAGGGAAG CAGAGACTTT CAAGGAACAA GGAAATGCAT ACTATGCCAA GAAAGATTAC    180

AATGAAGCTT ATAATTATTA TACAAAAGCC ATAGATATGT GTCCTAAAAA TGCTAGCTAT    240

TATGGTAATC GAGCAGCCAC CTTGATGATG CTTGGAAGGT TCCGGGAAGC TCTTGGAGAT    300

GCACAACAGT CAGTGAGGTT GGATGACAGT TTTGTCCGGG ACATCTACG AGAGGGCAAG     360

TGCCACCTCT CTCTGGGGAA TGCCATGGCA GCATGTCGCA GCTTCCAGAG AGCCCTAGAA    420

CTGGATCATA AAAATGCTCA GGCACAACAA GAGTTCAAGA ATGCTAATGC AGTCATGGAA    480

TATGAGAAAA TAGCAGAAAC AGATTTTGAG AAGCGAGATT TCGGAAGGT TGTTTTCTGC     540

ATGGACCGTG CCCTAGAATT TGCCCCTGCC TGCCATCGCT TCAAAATCCT CAAGGCAGAA    600

TGTTTAGCAA TGCTGGGTCG TTATCCAGAA GCACAGTCTG TGGCTAGTGA CATTCTACGA    660

ATGGATTCCA CCAATGCAGA TGCTCTGTAT GTACGAGGTC TTTGCCTTTA TTACGAAGAT    720

TGTATTGAGA AGGCAGTTCA GTTTTTCGTA CAGGCTCTCA GGATGGCTCC TGACCACGAG    780

AAGGCCTGCA TTGCCTGCAG AAATGCCAAA GCACTCAAAG CAAAGAAAGA AGATGGGAAT    840

AAAGCATTTA AGGAAGGAAA TTACAAACTA GCATATGAAC TGTACACAGA AGCCCTGGGG    900

ATAGACCCCA ACAATATAAA AACAAATGCT AAACTCTACT GTAATCGGGG TACGGTTAAT    960
```

-continued

```
TCCAAGCTTA GGAAACTAGA TGATGCAATA GAAGACTGCA CAAATGCAGT GAAGCTTGAT    1020

GACACTTACA TAAAAGCCTA CTTGAGAAGA GCTCAGTGTT ACATGGACAC AGAACAGTAT    1080

GAAGAAGCAG TACGAGACTA TGAAAAAGTA TACCAGACAG AGAAACAAA AGAACACAAA    1140

CAGCTCCTAA AAAATGCGCA GCTGGAACTG AAGAAGAGTA AGAGGAAAGA TTACTACAAG    1200

ATTCTAGGAG TGGACAAGAA TGCCTCTGAG GACGAGATCA AGAAAGCTTA TCGGAAACGG    1260

GCCTTGATGC ACCATCCAGA TCGGCATAGT GGAGCCAGTG CTGAGGTTCA GAAGGAGGAG    1320

GAGAAGAAGT TCAAGGAAGT TGGAGAGGCC TTTACTATCC TCTCTGATCC CAAGAAAAAG    1380

ACTCGCTATG ACAGTGGACA GGACCTAGAT GAGGAGGGCA TGAATATGGG TGATTTTGAT    1440

CCAAACAATA TCTTCAAGGC ATTCTTTGGC GGTCCTGGCG GCTTCAGCTT TGAAGCATCT    1500

GGTCCAGGGA ATTTCTTTTT TCAATTTGGC TAATGAAGGG CAACCACCCA GAACCCAGAA    1560

AATGCAGATT CACTCAGTTT AATCTTGAAT GTGGAAACAG TTCACCTCCT CCCTTCATCA    1620

CGTCTCCGTG TGCTTAGAGC AGTTTCGTTT TCTCAGTTGG ATGCCCTGTG TCTCTGTGAG    1680

TGGGGTGGAG CAAAGGGAAC CAATGCCGAA GACCGAGGGC AGGGGAGGGA GGCGGGGGTG    1740

GACAGGGAGG CAGCTTGTGA ATTTTTGTTT TACTGTTTAA CTTTATTAAA AAGAAAAAA    1800

AAAAAGAGAG A                                                        1811
```

(2) INFORMATION FOR SEQ ID NO:6:

(i) SEQUENCE CHARACTERISTICS:
        (A) LENGTH: 504 amino acids
        (B) TYPE: amino acid
        (C) STRANDEDNESS: single
        (D) TOPOLOGY: linear (vii) IMMEDIATE SOURCE:
        (A) LIBRARY: COLNNOT11
        (B) CLONE: 701698

(xi) SEQUENCE DESCRIPTION: SEQ ID NO:6:

```
Met Val Ala Pro Gly Ser Val Thr Ser Arg Leu Gly Ser Val Phe Pro
  1               5                  10                  15

Phe Leu Leu Val Leu Val Asp Leu Gln Tyr Glu Gly Ala Glu Cys Gly
                 20                  25                  30

Val Asn Ala Asp Val Glu Lys His Leu Glu Leu Gly Lys Lys Leu Leu
             35                  40                  45

Ala Ala Gly Gln Leu Ala Asp Ala Leu Ser Gln Phe His Ala Ala Val
         50                  55                  60

Asp Gly Asp Pro Asp Asn Tyr Ile Ala Tyr Tyr Arg Arg Ala Thr Val
 65                  70                  75                  80

Phe Leu Ala Met Gly Lys Ser Lys Ala Ala Leu Pro Asp Leu Thr Lys
                 85                  90                  95

Val Ile Glu Leu Lys Met Asp Phe Thr Ala Ala Arg Leu Gln Arg Gly
            100                 105                 110

His Leu Leu Lys Gln Gly Lys Leu Asp Glu Ala Glu Asp Asp Phe
        115                 120                 125

Lys Lys Val Leu Lys Ser Asn Pro Ser Glu Asn Glu Lys Glu Ala
    130                 135                 140

Gln Ser Gln Leu Val Lys Ser Asp Glu Met Gln Arg Leu Arg Ser Gln
145                 150                 155                 160

Ala Leu Asp Ala Phe Glu Ser Ser Asp Phe Thr Ala Ala Ile Thr Phe
                165                 170                 175

Leu Asp Lys Ile Leu Glu Val Cys Val Trp Asp Ala Glu Leu Arg Glu
```

```
                    180                 185                 190
Leu Arg Ala Glu Cys Phe Ile Lys Glu Gly Glu Pro Arg Lys Ala Ile
                195                 200                 205

Ser Asp Leu Lys Ala Ser Ser Lys Leu Lys Asn Asp Asn Thr Glu Ala
        210                 215                 220

Phe Tyr Lys Ile Ser Thr Leu Tyr Tyr Glu Leu Gly Asp His Glu Leu
225                 230                 235                 240

Ser Leu Ser Glu Val Arg Glu Cys Leu Lys Leu Asp Gln Asp His Lys
                245                 250                 255

Arg Cys Phe Ala His Tyr Lys Gln Val Lys Lys Leu Asn Lys Leu Ile
                260                 265                 270

Glu Ser Ala Glu Glu Leu Ile Lys Glu Gly Arg Tyr Thr Asp Ala Ile
                275                 280                 285

Ser Lys Tyr Glu Ser Val Met Lys Thr Glu Pro Gly Val His Glu Tyr
        290                 295                 300

Thr Ile Arg Ser Lys Glu Arg Ile Cys His Cys Phe Ser Lys Asp Glu
305                 310                 315                 320

Lys Pro Val Glu Ala Ile Arg Val Cys Ser Glu Val Leu Gln Val Glu
                325                 330                 335

Pro Asp Asn Val Asn Ala Leu Lys Asp Arg Ala Glu Ala Tyr Leu Ile
                340                 345                 350

Glu Glu Met Tyr Asp Glu Ala Ile Gln Asp Tyr Glu Thr Ala Gln Glu
                355                 360                 365

His Asn Glu Asn Asp Gln Gln Ile Arg Glu Gly Leu Glu Lys Ala Gln
        370                 375                 380

Arg Leu Leu Lys Gln Ser Gln Arg Arg Asp Tyr Tyr Lys Ile Leu Gly
385                 390                 395                 400

Val Lys Arg Asn Ala Lys Lys Gln Glu Ile Ile Lys Ala Tyr Arg Lys
                405                 410                 415

Leu Ala Leu Gln Trp His Pro Asp Asn Phe Gln Asn Glu Glu Glu Lys
                420                 425                 430

Lys Lys Ala Glu Lys Lys Phe Ile Asp Ile Ala Ala Ala Lys Glu Val
                435                 440                 445

Leu Ser Asp Pro Glu Met Arg Lys Lys Phe Asp Asp Gly Glu Asp Pro
        450                 455                 460

Leu Asp Ala Glu Ser Gln Gln Gly Gly Gly Gly Asn Pro Phe His Arg
465                 470                 475                 480

Ser Trp Asn Ser Trp Gln Gly Phe Ser Pro Phe Ser Gly Gly Pro
                485                 490                 495

Phe Arg Phe Lys Phe His Phe Asn
            500

(2) INFORMATION FOR SEQ ID NO:7:

(i) SEQUENCE CHARACTERISTICS:
        (A) LENGTH: 78 amino acids
        (B) TYPE: amino acid
        (C) STRANDEDNESS: single
        (D) TOPOLOGY: linear (vii) IMMEDIATE SOURCE:
        (A) LIBRARY: SYNORAT03
        (B) CLONE: 994480

(xi) SEQUENCE DESCRIPTION: SEQ ID NO:7:

Met Arg Thr Asp Ser Ser Lys Met Thr Asp Val Glu Ser Gly Val Ala
1               5                   10                  15
```

```
Asn Phe Ala Ser Ser Ala Arg Ala Gly Arg Arg Asn Ala Leu Pro Asp
                20                  25                  30

Ile Gln Ser Ser Ala Ala Thr Asp Gly Thr Ser Asp Leu Pro Leu Lys
        35                  40                  45

Leu Glu Ala Leu Ser Val Lys Glu Asp Ala Lys Glu Lys Asp Glu Lys
    50                  55                  60

Thr Thr Gln Asp Gln Leu Glu Lys Pro Gln Asn Glu Glu Lys
65                  70                  75

(2) INFORMATION FOR SEQ ID NO:8:

(i) SEQUENCE CHARACTERISTICS:
        (A) LENGTH: 710 base pairs
        (B) TYPE: nucleic acid
        (C) STRANDEDNESS: single
        (D) TOPOLOGY: linear (vii) IMMEDIATE SOURCE:
        (A) LIBRARY: SYNORAT03
        (B) CLONE: 994480

(xi) SEQUENCE DESCRIPTION: SEQ ID NO:8:

TGATTAGACT CTCAAGCCTG TTGTGTTTTT GATCTAGCCA TGCCTTTCAA CCACTGTGGT    60

GAACATTTAG CTCTGAATAG GCTCATCTTC TTCATATGCA CATTCTATTT GTAGATGTTG   120

CTATGAGGAC AGATTCATCA AAAATGACTG ACGTGGAGTC TGGGGTCGCC AATTTTGCAT   180

CTTCAGCAAG GGCAGGCCGC CGGAATGCCT TACCAGACAT CCAGAGTTCA GCTGCCACAG   240

ACGGAACCTC AGATTTGCCC CTCAAACTGG AGGCTCTCTC CGTGAAGGAA GATGCAAAAG   300

AGAAAGATGA AAAAACAACA CAAGACCAAT TGGAAAAGCC TCAAAATGAA GAAAAATGAA   360

GGCTCATAAT CTATCAAGAG TGCTGAATTT CTGCATGTTG AAAGACTTAG TGGTTCTGTT   420

TTCTTGAGAC ATTTAATCTG GTGRTAACTG TGGTAACATT GCAGCCCTAA GCAGCATGTG   480

TATATTAGAT AATTGTGTTG TGATGCTACT CACTTTGATT GCAATGATGA TGTCCAAGGT   540

AAGCTATTAA AAGGCAGGTT ACTTCCAAAT CGCACTGAAG GAAAAGGTTA AGAATAATAC   600

ATGATCACAG AAATGCATAC CACTGTCTGT AAACCCAACA AAATTCACTG TTCTCTTTTG   660

GATTTATTTA GCCTGATGTA TTTTTAATTC AATTTTTATG GTGATGGGCA             710

(2) INFORMATION FOR SEQ ID NO:9:

(i) SEQUENCE CHARACTERISTICS:
        (A) LENGTH: 92 amino acids
        (B) TYPE: amino acid
        (C) STRANDEDNESS: single
        (D) TOPOLOGY: linear (vii) IMMEDIATE SOURCE:
        (A) LIBRARY: 994480
        (B) CLONE: SYNORAT03

(xi) SEQUENCE DESCRIPTION: SEQ ID NO:9:

Met Gly Gly Gly Thr Ser Pro Glu Ala Gln Gln Asp Ser Val Met Arg
1               5                   10                  15

Thr Asp Ser Ser Glu Met Thr Asp Val Glu Ser Val Ile Thr Ser Phe
                20                  25                  30

Ala Ser Ser Ala Arg Ala Gly Arg Arg Asn Ala Leu Pro Asp Ile Gln
        35                  40                  45

Ser Ser Leu Ala Thr Ser Gly Ser Asp Leu Pro Leu Lys Leu Glu
    50                  55                  60
```

```
-continued

Ala Leu Ala Val Lys Glu Asp Ala Lys Thr Lys Asn Glu Glu Lys Asp
65                  70                  75                  80

Gln Gly Gln Pro Lys Thr Pro Leu Asn Glu Gly Lys
                85                  90
```